US005512455A

United States Patent [19]

Schenk

[11] Patent Number: 5,512,455

[45] Date of Patent: Apr. 30, 1996

[54] ATRIAL NATRIURETIC PEPTIDE RECEPTOR PROTEIN

[75] Inventor: Dale B. Schenk, Campbell, Calif.

[73] Assignee: Scios Nova, Inc., Mountain View, Calif.

[21] Appl. No.: 48,296

[22] Filed: May 11, 1987

Related U.S. Application Data

[63] Continuation-in-part of Ser. No. 861,529, May 9, 1986, abandoned.

[51] Int. Cl.[6] .............................. C12P 21/02; C12N 1/21; C12N 5/10; C12N 15/12; C12N 15/70

[52] U.S. Cl. .................... 435/69.1; 536/23.5; 435/310.1; 435/252.3; 435/252.33; 435/240.2; 435/172.3; 935/73; 935/9; 935/29; 935/32; 935/70; 930/50

[58] Field of Search ................................. 435/68, 70, 91, 435/172.1, 172.3, 240.1, 252.3, 252.33, 320, 320.1; 536/27; 530/350

[56] References Cited

U.S. PATENT DOCUMENTS

| | | | |
|---|---|---|---|
| 4,394,443 | 6/1983 | Weissman et al. | 435/6 |
| 4,562,003 | 12/1985 | Lewicki | 436/520 |
| 4,578,335 | 3/1986 | Urdal et al. | 435/70.4 |
| 4,761,371 | 8/1988 | Bell et al. | 435/68.1 |

OTHER PUBLICATIONS

*Stedtman's Medical Dictionary,* 25th Edition, 1990, Williams and Wilkins. Baltimore, p. 1327.
Lewin, R. 1987. Science. 237, 1570.
Reeck et al., 1987 Cell 50, 667.
Rogers, T. B. 1984, J. Biol. Chem. 259, 8106–8114.
Lesk, A. M. (ed.) in: Computational Molecular Biology Sources and Methods for Sequence Analysis. Oxford Univ. Press. Oxford, pp. 161–163.
Janson, J. C. 1984 Trends Biotechnol. 2, 31–38.
Gerhardt et al. 1981 in: *Manual of Methods for general Bacteriology* Am. Soc. for Mircobiology. Washington D.C. pp. 304–305.
Cooper, T. G. 1977 in: *The Tools of Biochemistry.* John Wiley and Sons. New York. pp. 234–255, and 355–405.
Baker et al. 1982. in: *Fourth Edition. The Study of Biology.* Addison–Wesley Publ. Co. Reading, Mass. pp. 922–924.
Wallace et al. 1981, Nucliec Acids. Res. 9, 879–894.
Jaye et al. 1983. Nucleic Acids Res. 11, 2325–2324.
Maniatis et al. 1982. in: Molecular Cloning. A. Laboratory Manual, Cold Spring Harbor Laboratories, Cold Spring Harbor Laboratory, N.Y. pp. 270–320, 188–228.
Carrier et al (1985) Biochem. Biophys. Res. Comm. 132:666–673.
David L. Urdal et al, (1984) Proc. Nat'l. Acad. Sci., USA 81:6481–6485.
Cosman et al, (1984) Nature 312:768–771.
Uchiyama et al, (1981) The journal of Immunology 126:1393–1397.
DeBold et al, (1981) Life Sci. 28:89–94.
Napier et al, (1984) Ann. Rep. Med. Chem. 19:253–262.
Kangawa et al., (1984) Biochem. Biophys. Res. Commun. 118:131–139.
Flynn et al., (1983) Biochem. Biophys. Res. Commun. 117:859–865.
Napier et al., (1984) Biochem. Biophys. Res. Commun. 120:981–988.
Currie et al., (1984) Science 223:67–69.
Thibault et al., (1984) FEBS Lett. 167:352–356.
Atlas et al, (1984) Nature vol. 309:717–719.
Yamanaka et al., (1984) Nature vol. 309:719–722.
Kuno et al., (1986) J. Biol. Chem. 261:5817–5823.
Leitman et al., (1986) Biochim. Biophys. Acta 885: 74–79.
De Lean et al., (1984) Endocrinology 115:1636–1638.
De Lean et al., (1984) Life Sci. 35:2311–2318.
Flynn et al., (1985) Science 228:323–325.
Gutkowska et al., (1984) Biochem. Biophys. Res. Common. 125:315–323.
Hirata et al., (1984) Biochem. Biophys. Res. Commun. 125:562–568.
Hirata et al., (1985) Biochem. Biophys. Res. Commun. 128:538–546.
Hirose et al., (1985) Biochem. Biophys. Res. Commun. 130:574–579.
Nutt, R. P., et al., In Peptides 1984 (U. Ragnarsson ed. 1985.
Oikawa et al., (1984) Nature 309:724–726.
Petruzzelli et al., (1984) Proc. Natl. Acad. Sci. USA 81:3327–3331.
Schenk et al. (II), (1985) Biochem. Biophys. Res. Commun. 127:433–442.
Schenk et al. (I). (1985) J. Biol. Chem. 260:14887–14890.
Schneider et al., (1982) J. Biol. Chem. 257:2664–2673.
Seidah et al., (1984) Proc. Natl. Acad. Sci. USA 81:2640–2644.
Seidman et al., (1984) Science 225:324–326.
Tanaka et al., (1984) Biochem. Biophys. Res. Commun. 124:663–668.
Vandlen et al., (1985) J. Biol. Chem. 260:10889–10892.
Wimalasena et al., (1985) J. Biol. Chem. 260:10689–10697.
Winquist et al., (1984) Proc. Natl. Acad. Sci. USA 81:7661–7664.
Yip et al., (1985) J. Biol. Chem. 260:8229–8232.
Hayashi et al. (1986) Peptide Chemistry 1985, pp. 27–32.
Scarborough et al. (1986) J. Biol. Chem. 261: 12960–12964.
Leitman et al. (1986) J. Biol. Chem. 261: 11650–11655.
Hirata et al. (1985) Biochem. Biophys. Res. Comm. 132: 976–984.
Napier et al. (1986) Arch. Biochem. Biophys. 248: 516–522.

*Primary Examiner*—Christopher S. F. Low
*Attorney, Agent, or Firm*—Morrison & Foerster

[57] ABSTRACT

Purified native Atrial Naturetic Peptide (ANP) receptor protein is provided, as well as synthetic ANP receptor and methods of making and using ANP receptor protein and antibodies.

10 Claims, 14 Drawing Sheets

```
Ixx Ala Leu Pro Pro Gln Lys Ile Glu Val Leu Val Leu Leu Pro Gln Asp
    Asp Ser Tyr Leu Phe Ser Leu Ala Arg Val Arg Pro Ala Ile Glu

1. GTT TTT TAT CTT CA                2. GTT CTA CTA AGA AT
     C   C   A   C                         C   G   G   G
             G                                         C
                                                       T
                                                     TCA
                                                       G

                 *                   *
3. GTC TTC TA[G] CTC CAC GAC CAC GAC GAC GGG GTC CT[G] CTG AGG ATG GAC AAG
              A                                     A      TCG
```

FIG. 2A

```
  1  GCGCGAATCA ATGAGATCAA ACGCGAGGGA GATGCACCGT CAATTACAAG CACTTGGACA AGTCTAACTT TTTCTTCTTT TACAAATGCT  90
 91  CTTTCCAAAG CAACCTTAGC AACGCCATAT AAGAAGCCAC CTCTAAGCAA AATAGCTATA TATCAAGGGA GGGCTAATCT ATGTATTTAT 180
181  AAAAAGTATA TATATATAAA TATACTATAG GAGTACAGGT TTACACCCAG TTAACTTTTT CTTTTTCTTT CTGTCTTCTT TCTTTTTTTT 270
271  TTTTAAACGA GTGGCATTGC AAAGGAGGAC TCTTCCTCTC TTTTGGCGAG TTAGTGAAGG GGGTATTCTT TTATTTTTTC TTAGAGCGCC 360
361  CAAGGGGCGC AGGAACCTCG GAGAGGAGTT GGGGAGTTAA GAGGTAGGGT GGGTGGGGGG CAGAGGGCGA GTCCGCAGCG AGGGCAGGCG 450
451  CTTTCCTGCGGCACG ATG CCG TCC CTA CTG GTG CTC ACT TTC TCC GCG TGC GTC CTG CTC GGT TGG GCG TTA CTG     525
                 MET Pro Ser Leu Leu Val Leu Thr Phe Ser Ala Cys Val Leu Leu Gly Trp Ala▲Leu Leu
                 001
526  GCC GAC TGC ACT GGC GGC GGT GGC AGC GGG GGC GCG GGC CCG GGC CGC GGG CGC CGG GAG AGA GAG GCA CTG CCG 600
     Ala Asp Cys Thr Gly Gly Gly Gly Ser Gly Gly▲Ala Gly Pro Gly Arg Gly Arg Arg Glu Arg▲Glu Ala Leu Pro

601  CCG CAG AAG ATC GAG GTT CTG GTG CTG TTG CCC CAG GAC GAC TCT TAC CTG TTC TCC CTT GCT CGG GTG CGA CCG 675
     Pro Gln Lys Ile Glu Val Leu Val Leu Leu Pro Gln Asp Asp Ser Tyr Leu Phe Ser Leu Ala Arg Val Arg Pro
                 050
676  GCC ATA GAG TAC GCG CTG CGC ACG GTG GAG GGC AAC GCG ACC GGG CGG CGG CTC CTG CCA GCC GGC ACT CGC TTC 750
     Ala Ile Glu Tyr Ala Leu Arg Thr Val Glu Gly[Asn Ala Thr]Gly Arg Arg Leu Leu Pro Ala Gly Thr Arg Phe

751  CAG GTG GCC TAC GAA GAC TCG GAC TGC GGC AAC CGC GCA CTC TTC AGC CTG GTG GAC CGC GTG GCG GCG GCG CGG 825
     Gln Val Ala Tyr Glu Asp Ser Asp Cys Gly Asn Arg Ala Leu Phe Ser Leu Val Asp Arg Val Ala Ala Ala Arg
                 100
826  GGA GCC AAG CCG GAT CTC ATC CTG GGG CCG GTG TGC GAG TAC GCG GCG GCG CCG GTG GCT CGG CTA GCG TCG CAC 900
     Gly Ala Lys Pro Asp Leu Ile Leu Gly Pro Val Cys Glu Tyr Ala Ala Ala Pro Val Ala Arg Leu Ala Ser His

901  TGG GAC CTC CCC ATG CTG TCT GCC GGG GCC CTG GCA GCC GGC TTC CAG CAT AAG GAC ACG GAG TAC TCG CAC CTT 975
     Trp Asp Leu Pro MET Leu Ser Ala Gly Ala Leu Ala Ala Gly Phe Gln His Lys Asp Thr Glu Tyr Ser His Leu
                 150
976  ACG CGC GTG GCA CCC TCG TAC GCC AAG ATG GGC GAG ATG ATG CTC GCC CTG TTC CGC CAC CAC CAG TGG AGC CGC 1050
     Thr Arg Val Ala Pro Ser Tyr Ala Lys MET Gly Glu MET MET Leu Ala Leu Phe Arg His His Gln Trp Ser Arg
```

FIG. 3A

```
1051 GCC GTG CTG GTC TAC AGC GAC GAC AAG CTG GAG CGG AAC TGC TTC TTC ACC CTC GAG GGG GTC CAT GAG GTC TTC 1125
     Ala Val Leu Val Tyr Ser Asp Asp Lys Leu Glu Arg Asn Cys Phe Phe Thr Leu Glu Gly Val His Glu Val Phe
                     200
1126 CAG GAG GAA GGC TTG CAC ACG TCC GCC TAC AAT TTC GAT GAG ACC AAA GAC TTG GAT CTG GAG GAC ATC GTG CGC 1200
     Gln Glu Glu Gly Leu His Thr Ser Ala Tyr Asn Phe Asp Glu Thr Lys Asp Leu Asp Leu Glu Asp Ile Val Arg

1201 CAC ATC CAG GCC AGT GAG CGA GTG GTG ATC ATG TGT GCG AGT AGC GAC ACC ATC CGG GGG ATC ATG CTG GCG GCG 1275
     His Ile Gln Ala Ser Glu Arg Val Val Ile MET Cys Ala Ser Ser Asp Thr Ile Arg Gly Ile MET Leu Ala Ala
                     250
1276 CAC AGG CAC GGA ATG ACC AGC GGG GAC TAC GCC TTC TTC AAC ATC GAG CTC TTC AAC AGC TCC TTC TAT GGA GAT 1350
     His Arg His Gly MET Thr Ser Gly Asp Tyr Ala Phe Phe Asn Ile Glu Leu Phe[Asn Ser Ser]Phe Tyr Gly Asp

1351 GGC TCG TGG AAG AGA GGA GAC AAA CAC GAC TTT GAA GCT AAG CAA GCG TAC TCA TCC CTC CAA ACA ATC ACT CTA 1425
     Gly Ser Trp Lys Arg Gly Asp Lys His Asp Phe Glu Ala Lys Gln Ala Tyr Ser Ser Leu Gln Thr Ile Thr Leu
                     300
1426 CTG AGG ACA GCG AAA CCT GAG TTT GAG AAG TTT TCC ATG GAG GTG AAA AGT TCT GTT GAG AAG CAA GGG CTC AGT 1500
     Leu Arg Thr Ala Lys Pro Glu Phe Glu Lys Phe Ser MET Glu Val Lys Ser Ser Val Glu Lys Gln Gly Leu Ser

1501 GAG GAA GAT TAC GTG AAC ATG TTT GTT GAA GGA TTC CAC GAT GCC ATC CTC CTC TAC GTC CTG GCT TTA CGT GAA 1575
     Glu Glu Asp Tyr Val Asn MET Phe Val Glu Gly Phe His Asp Ala Ile Leu Leu Tyr Val Leu Ala Leu Arg Glu
                     350
1576 GTA CTC AGA GCT GGT TAC AGT AAG AAG GAT GGA GGG AAA ATT ATC CAG CAG ACT TGG AAC CGA ACA TTT GAA GGT 1650
     Val Leu Arg Ala Gly Tyr Ser Lys Lys Asp Gly Gly Lys Ile Ile Gln Gln Thr Trp Asn Arg Thr Phe Glu Gly

1651 ATT GCT GGG CAG GTC TCC ATA GAT GCC AAC GGA GAC CGG TAT GGG GAT TTC TCT GTG ATC GCC ATG ACT GAC ACA 1725
     Ile Ala Gly Gln Val Ser Ile Asp Ala Asn Gly Asp Arg Tyr Gly Asp Phe Ser Val Ile Ala MET Thr Asp Thr
                     400
1726 GAA GCG GGT ACC CAG GAG GTT ATT GGT GAT TAC TTT GGA AAA GAA GGT CGT TTT GAA ATG CGG CCG AAT GTC AAA 1800
     Glu Ala Gly Thr Gln Glu Val Ile Gly Asp Tyr Phe Gly Lys Glu Gly Arg Phe Glu MET Arg Pro Asn Val Lys
```

FIG. 3B

```
1801 TAT CCT TGG GGA CCT TTA AAA CTG AGA ATA GAT GAA ACC AGA ATG GTG GAG CAC ACG AAC AGC TCT CCT TGC AAA 1875
     Tyr Pro Trp Gly Pro Leu Lys Leu Arg Ile Asp Glu Thr Arg MET Val Glu His Thr Asn Ser Ser Pro Cys Lys
                     450
1876 GCA TCA GGT GGC CTA GAA GAA TCA GCG GTG ACA GGA ATT GTT GTG GGG GCC TTA CTA GGA GCT GGT TTG CTA ATG 1950
     Ala Ser Gly Gly Leu Glu Glu Ser Ala Val Thr Gly Ile Val Val Gly Ala Leu Leu Gly Ala Gly Leu Leu MET

1951 GCC TTC TAC TTC TTC AGG AAG AAA TAC AGA ATA ACC ATT GAG AGG CGA AAC CAG CAA GAA GAA AGC AAC GTT GGA 2025
     Ala Phe Tyr Phe Phe Arg Lys Lys Tyr Arg Ile Thr Ile Glu Arg Arg Asn Gln Gln Glu Glu Ser Asn Val Gly
                         501
2026 AAA CAT CGG GAG TTA CGG GAA GAT TCC ATC AGA TCC CAC TTT TCG GTG GCT TAA AAGGAAGTCTG TTCTTTTGGC     2100
     Lys His Arg Glu Leu Arg Glu Asp Ser Ile Arg Ser His Phe Ser Val Ala End

2101 TTGAGATTCT TTAAGGAGAT AGATGGGATG AAAGACATCA ATGGAATAGA AGGGGCGCTC TTGAAAAACT CATTCTTTTA AGCAGTTAGT 2190
2191 AATTTTGTTA TAAAATTTCT TTAGAAGCTC AGGAACTATT ATTAATCACC ATATGCCCGC TGGCCTCTCA TCTCATGACA AACAAACACA 2280
2281 AGAATATAAC ATCACTCCTA AATGTTGATT CTGTTTCAAG GGCATATGAT TAGATTTATG TTCTGAAAGT CTGAGGTCTC CATATCTTGT 2370
2371 TGGCGTTTGG GGGCATTTTA CACAAGGCTA TAAAATGTGT TTTACTTAAG TGAGATGTTT TATAGCTAGA ATAAAATCAT TTTTACATGT 2460
2461 AGGATATTAT TGAAAAGGAT TTAACCCCAA GAAGAAGAAA ATGTAATGGA AAACCTCAAG GTTGAAAATG CAGCATTCCT CTCTCTAGAG 2550
2551 CTGGTTGGAG GGATCTGAGG TCAAGGGGCT TCTATCTGAT ATATGCATTC ACATCCTGAC TTTATGTTTG AAAAAGAATT TCCCCCACCT 2640
2641 CTTTCAGTGT CTTGTAAGAG CTACTTTGGA AAGTTGTAAT TATGAATGAG ATAAGAGGAT TTATGCAGAA AAAGCAAATC TAACTATTTC 2730
2731 ACTTTTTAAA ATATAAAAAA CCCTATTTCA CACTAACATT TTATTTTTAA GTATTTTAAT CTTATATTTT CCTATTAGAA AATGTGTCTA 2820
```

FIG. 3C

```
2821 TTTTTTCATT TTGAAGATTA AATTTCACTT ATATTTTAAA AACATGGGTA ATGTGTACAG CAAACCCAAT AATGATGAAA GGATGCCCTC 2910
2911 TCTTTTTTTC TCCCTGTTTC CCTCTTCCCT GTGGCCATAG CCCAATACGA ATTGCTGCTT GAACTACAGA GATCTAGAAA TGTGTTCGGA 3000
3001 TTGTAGACTC TACAGGAATA CATCAGTTTA CTTGTTTTAA ATGCAAGCTA TTTTAGGATA GTCTCCTTCC AGTTCTGGCC AAAGGATGAA 3090
3091 ATTTATTAGA ATTAAGTCAG GTTTTATAAA GGGAGGCAAC CTTTTTTTCT CAAGAAGAAC TTTATAGAGA GTTAGAACTT GGCAGTACGC 3180
3181 ATAGAAATGA TAATTTAATA AATGACATTT TACCAAAATT GACGATTATG ATTTTGGTTA AAAGAGGGAA TCTAAACAGC TACTATGTTC 3270
3271 CCTTTTAGTA AACACCGCAG AACTTTGCAG TCATCCACTA ATAACTTGTG TAACAGGGGT TGGGTACGGA TATCAGGAAT TGGTCAAGGT 3360
3361 TGAATAATTA TTTGCCGAAT CTCAACTTTG CACCAAGTAC TCTGTGTATA GGTAGGTTTA AGCTTAGGTT GCCACTTTCA TGTATAATTT 3450
3451 GTGGAGAAAA CAGACAGTGA GGGAAGAATG GGAAGTTGCC AGATCGGTGT ACTATCTTAT AATGATATCA TGAAGGTGCT TCCTCAATAA 3540
3541 TGTTTGGAGC ATCTGGAA 3558
```

FIG. 3D

```
        10         20         30         40         50         60         70
GAATTCGCAT GGTCGACTAC ACGCCCAAAT AAGAAGCCAC CTCTAAGCAA AATAGCTATA TGTATAAACG

        80         90        100        110        120        130        140
GAGGGCGAAT ATATACAAGT ATATATATAT GTATATTACA GACGCACAGG TTTACACCCG GTGAACTTTT

       150        160        170        180        190        200        210
TCTTTTTCTT TTTCTTTTTC CTTTTTTTTT AAGAAAAACT AGTGACATTG CAGAGAAGGA CGCTTCCTCT

       220        230        240        250        260        270        280
CTATCTTTTG GCGCATTAGT GAAGGGGGTA TTCTATTTTG TTAAAGCGCC CAAGGGGACC GGGAACCTTG

       290        300        310        320        330        340        350
GAGAGAAGAG TGGGGAGGAA AGAGGAAGGG TGGGTGGGGG GCAGAGGGCG AGTCGGCGGC GGCGAGGGCA

       360                            384             399
AGCTCTTTCT TGCGGCACG ATG CCG TCT CTG CTG GTG CTC ACT TTC TCC CCG TGC GTA
                     MET Pro Ser Leu Leu Val Leu Thr Phe Ser Pro Cys Val
   414                 429                 444                 459
CTA CTC GGC TGG GCG TTG CTG GCC GGC GGC ACC GGT GGC GGT GGC GTT GGC GGC
Leu Leu Gly Trp Ala Leu Leu Ala Gly Gly Thr Gly Gly Gly Gly Val Gly Gly
```

FIG. 5A

```
                474                     489                     504
GGC GGC GGT GGC GCG GGC ATA GGC GGC GGA CGC CAG GAG AGA GAG GCC GTG CCG
Gly Gly Gly Gly Ala Gly Ile Gly Gly Gly Arg Gln Glu Arg Glu Ala Val Pro

519                 534                     549                 564
CCA CAG AAG ATC GAG GTG CTG GTG TTA CTG CCC CAG GAT GAC TCG TAC TTG TTT
Pro Gln Lys Ile Glu Val Leu Val Leu Leu Pro Gln Asp Asp Ser Tyr Leu Phe

        579                     594                     609                 624
TCA CTC ACC CGG GTG CGG CCG GCC ATC GAG TAT GCT CTG CGC AGC GTG GAG GGC
Ser Leu Thr Arg Val Arg Pro Ala Ile Glu Tyr Ala Leu Arg Ser Val Glu Gly

                639                     654                     669
AAC GGG ACT GGG AGG CGG CTT CTG CCG CCG GGC ACT CGC TTC CAG GTG GCT TAC
Asn Gly Thr Gly Arg Arg Leu Leu Pro Pro Gly Thr Arg Phe Gln Val Ala Tyr

    684                     699                     714                     729
GAG GAT TCA GAC TGT GGG AAC CGT GCG CTC TTC AGC TTG GTG GAC CGC GTG GCG
Glu Asp Ser Asp Cys Gly Asn Arg Ala Leu Phe Ser Leu Val Asp Arg Val Ala

            744                     759                     774
GCG GCG CGG GGC GCC AAG CCA GAC CTT ATC CTG GGG CCA GTG TGC GAG TAT GCA
Ala Ala Arg Gly Ala Lys Pro Asp Leu Ile Leu Gly Pro Val Cys Glu Tyr Ala
```

FIG. 5B

```
789                     804                     819                     834
GCA GCG CCA GTG GCC CGG CTT GCA TCG CAC TGG GAC CTG CCC ATG CTG TCG GCT
Ala Ala Pro Val Ala Arg Leu Ala Ser His Trp Asp Leu Pro MET Leu Ser Ala

        849                     864                     879                     894
GGG GCG CTG GCC GCT GGC TTC CAG CAC AAG GAC TCT GAG TAC TCG CAC CTC GAG
Gly Ala Leu Ala Ala Gly Phe Gln His Lys Asp Ser Glu Tyr Ser His Leu Glu

                909                     924                     939
CGC GTG GCG CCC GCC TAC GCC AAG ATG GGC GAG ATG ATG CTC GCC CTG TTC CGC
Arg Val Ala Pro Ala Tyr Ala Lys MET Gly Glu MET MET Leu Ala Leu Phe Arg

    954                     969                     984                     999
CAC CAC CAC TGG AGC CGC GCT GCA CTG GTC TAC AGC GAC GAC AAG CTG GAG CGG
His His His Trp Ser Arg Ala Ala Leu Val Tyr Ser Asp Asp Lys Leu Glu Arg

           1014                    1029                    1044
AAC TGC TAC TTC ACC CTC GAG GGG GTC CAC GAG GTC TCC CAG GAG GAG GGT TTG
Asn Cys Tyr Phe Thr Leu Glu Gly Val His Glu Val Ser Gln Glu Glu Gly Leu

1059                   1074                    1089                    1104
CAC ACG TCC ATC TAC AGT TTC GAC GAG ACC AAA GAC TTG GAT CTG GAA GAC ATC
His Thr Ser Ile Tyr Ser Phe Asp Glu Thr Lys Asp Leu Asp Leu Glu Asp Ile

       1119                    1134                    1149                    1164
CTG CGC AAT ATC CAG GCC AGT GAG AGA GTG GTG ATC ATG TGT GCG AGC AGT GAC
Leu Arg Asn Ile Gln Ala Ser Glu Arg Val Val Ile MET Cys Ala Ser Ser Asp
```

FIG. 5C

```
                    1179                          1194                          1209
ACC ATC CGG AGC ATC ATG CTG GTG GCG CAC AGG CAT GGC ATG ACC AGT GGA GAC
Thr Ile Arg Ser Ile MET Leu Val Ala His Arg His Gly MET Thr Ser Gly Asp

    1224                          1239                          1254                          1269
TAC GCC TTC TTC AAC ATT GAG CTC TTC AAC AGC TCT TCC TAT GGA GAT GGC TCA
Tyr Ala Phe Phe Asn Ile Glu Leu Phe Asn Ser Ser Ser Tyr Gly Asp Gly Ser

            1284                          1299                          1314
TGG AAG AGA GGA GAC AAA CAC GAC TTT GAA GCT AAG CAA GCA TAC TCG TCC CTC
Trp Lys Arg Gly Asp Lys His Asp Phe Glu Ala Lys Gln Ala Tyr Ser Ser Leu

1329                          1344                          1359                          1374
CAG ACA GTC ACT CTA CTG AGG ACA GTG AAA CCT GAG TTT GAG AAG TTT TCC ATG
Gln Thr Val Thr Leu Leu Arg Thr Val Lys Pro Glu Phe Glu Lys Phe Ser MET

        1389                          1404                          1419                          1434
GAG GTG AAA AGT TCA GTT GAG AAA CAA GGG CTC AAT ATG GAG GAT TAC GTT AAC
Glu Val Lys Ser Ser Val Glu Lys Gln Gly Leu Asn MET Glu Asp Tyr Val Asn

                    1449                          1464                          1479
ATG TTT GTT GAA GGA TTC CAC GAT GCC ATC CTC CTC TAC GTC TTG GCT CTA CAT
MET Phe Val Glu Gly Phe His Asp Ala Ile Leu Leu Tyr Val Leu Ala Leu His
```

FIG. 5D

```
    1494                     1509                     1524                     1539
GAA GTA CTC AGA GCT GGT TAC AGC AAA AAG GAT GGA GGG AAA ATT ATA CAG CAG
Glu Val Leu Arg Ala Gly Tyr Ser Lys Lys Asp Gly Gly Lys Ile Ile Gln Gln

              1554                     1569                     1584
ACT TGG AAC AGA ACA TTT GAA GGT ATC GCC GGG CAG GTG TCC ATA GAT GCC AAC
Thr Trp Asn Arg Thr Phe Glu Gly Ile Ala Gly Gln Val Ser Ile Asp Ala Asn

1599                     1614                     1629                     1644
GGA GAC CGA TAT GGG GAT TTC TCT GTG ATT GCC ATG ACT GAT GTG GAG GCG GGC
Gly Asp Arg Tyr Gly Asp Phe Ser Val Ile Ala MET Thr Asp Val Glu Ala Gly

        1659                     1674                     1689                     1704
ACC CAG GAG GTT ATT GGT GAT TAT TTT GGA AAA GAA GGT CGT TTT GAA ATG CGG
Thr Gln Glu Val Ile Gly Asp Tyr Phe Gly Lys Glu Gly Arg Phe Glu MET Arg

                    1719                     1734                     1749
CCG AAT GTC AAA TAT CCT TGG GGC CCT TTA AAA CTG AGA ATA GAT GAA AAC CGA
Pro Asn Val Lys Tyr Pro Trp Gly Pro Leu Lys Leu Arg Ile Asp Glu Asn Arg

    1764                     1779                     1794                     1809
ATT GTA GAG CAT ACA AAC AGC TCT CCC TGC AAA TCA TCA GGT GGC CTA GAA GAA
Ile Val Glu His Thr Asn Ser Ser Pro Cys Lys Ser Ser Gly Gly Leu Glu Glu
```

FIG. 5E

```
          1824                        1839                        1854
TCG GCA GTG ACA GGA ATT GTC GTG GGG GCT TTA CTA GGA GCT GGC TTG CTA ATG
Ser Ala Val Thr Gly Ile Val Val Gly Ala Leu Leu Gly Ala Gly Leu Leu MET

1869                1884                        1899                        1914
GCC TTC TAC TTT TTC AGG AAG AAA TAC AGA ATA ACC ATT GAG AGG CGA ACC CAG
Ala Phe Tyr Phe Phe Arg Lys Lys Tyr Arg Ile Thr Ile Glu Arg Arg Thr Gln

        1929                        1944                        1959                        1974
CAA GAA GAA AGT AAC CTT GGA AAA CAT CGG GAA TTA CGG GAA GAT TCC ATC AGA
Gln Glu Glu Ser Asn Leu Gly Lys His Arg Glu Leu Arg Glu Asp Ser Ile Arg

                  1989          2002       2012       2022       2032       2042
TCC CAT TTT TCA GTA GCT TAAAGGAAGC CCCCCACTTT TTTTTTTCT GCCTGAGATT CTTTAAGGAG
Ser His Phe Ser Val Ala

       2052       2062       2072       2082       2092
ATAGACGGGT TGAAAGACAT CAATGAAACA GAAGGGGCGT TCTTGAAGAA TTC
```

FIG. 5F

ATRIAL NATRIURETIC PEPTIDE RECEPTOR PROTEIN

This application is a continuation-in-part application of Ser. No. 861,529, filed 9 May 1986 now abandoned.

TECHNICAL FIELD

The present invention relates to Atrial Natriuretic Peptide receptor protein, methods of producing both native and synthetic receptor protein, and methods of using the receptor protein.

BACKGROUND OF THE INVENTION

Atrial Natriuretic Peptide (ANP) is a potent natriuretic and vasorelaxant polypeptide which has been isolated from the extracts of mammalian atria. DeBold et al., (1981) Life Sci. 28:89–94; Napier et al., (1984) Ann. Rep. Med. Chem. 19:253–262; Kangawa et al., (1984) Biochem. Biophys. Res. Commun. 118:131–139; Flynn et al., (1983) Biochem. Biophys. Res. Commun. 117:859–865; Napier et al., (1984) Biochem. Biophys. Res. Commun. 120:981–988; Currie et al., (1984) Science 223:67–69; Thibault et al., (1984) FEBS Lett. 167:352–356; Atlas et al., (1984) Nature 309:717–719. These peptides have been given a variety of names (e.g., atriopeptins and cardionatrins), but are now collectively referred to as ANP.

It has been determined from the sequence of cloned cDNA for these peptides that they are all derived from the carboxy-terminal region of a precursor protein whose structure has been recently established. Yamanaka et al., (1984) Nature 309:719–722; Maki et al., (1984) Nature 309:722–724; Oikawa et al., (1984) Nature 309:724–726; Seidman et al., (1984) Science 22:324–326; Flynn et al., (1985) Science 228:323–325. The different sizes of ANP appears to be a result of a difference in post-translational processing or artifactual degradation during isolation. Several synthetic ANPs have also been prepared and shown to contain all the biological properties of the native peptides. Seidah et al., (1984) Proc. Natl. Acad. Sci. USA 81:2640–2644; R. P. Nutt et al., in PEPTIDES 1984 (U. Ragnarsson ed. 1985); Atlas et al., supra.

ANP has been shown to play a significant role in blood-pressure homeostasis, regulation of extracellular fluid volume, and as an antagonist to the hypertensive effects of the renin-angiotensin system and other hormonal and neurotransmitter systems. ANP has been detected in the blood by radioimmunoassay. Gutkowska et al., (1984) Biochem. Biophys. Res. Common. 125:315–323; Tanaka et al., (1984) Biochem. Biophys. Res. Commun. 124:663–668. The biological effects of ANP are mediated through the binding of ANP to specific receptors on cell membranes. The existence of specific receptors has been demonstrated in a variety of kidney, adrenal cortex and vascular tissue. Schenk et al. (1985) J. Biol. Chem. 260:14887–14890; Vandlen et al., (1985) J. Biol. Chem. 260:10889–10892; Misono et al., (1985) Biochem. Biophys. Res. Commun. 130:994–1001; Hirose et al., (1985) Biochem. Biophys. Res. Commun. 130:574–579; Yip et al., (1985) J. Biol. Chem. 260:8229–8232; Schenk et al. (II). (1985) Biochem. Biophys. Res. Commun. 127:433–442; Hirata et al., (1985) Biochem. Biophys. Res. Commun. 128:538–546; Winquist et al., (1984) Proc. Natl. Acad. Sci. USA 81:7661–7664; Napier et al., (1984) Proc. Natl. Acad. Sci. USA 81:5946–5950; Hirata et al., (1984) Biochem. Biophys. Res. Commun. 125:562–568; De Lean et al., Endocrinology 115:1636–1638; De Lean et al., (1984) Life Sci. 35:2311–2318.

Because of the potent biological activity of ANP, regulation of its levels in the blood would be a therapeutic approach to the treatment of such disorders as hypertension, shock, and the like. To establish therapeutic protocols, however, it is necessary to have a sensitive assay for determining the levels of ANP in the blood of mammals. Such an assay could also be used to diagnose ailments such as hypertension. ANP receptor protein, if available, could be readily employed in the these assays. While current native and synthetic ANP, as well as analogs thereof, would allow for the modulation of fluid volume and vascular function by increasing ANP levels, effective therapies may also require ANP levels to be reduced in order to achieve the desired extracellular fluid volume and electrolytic homeostasis. It is possible that soluble fractions of ANP receptor could be used therapeutically to reduce serum levels of ANP.

While various attempts have been made to characterize the ANP receptor, it has not been purified. Furthermore, these attempts at characterization have produced conflicting results. See, e.g., Schenk et al. (I), supra; Vandlen et al., supra; Misono et al., supra; Hirose et al., (1985), supra; Yip et al., supra.

Recent work has suggested that there may be more than one ANP receptor. See Leitman et al. (1986) Biochim. Biophys. Acta 885:74–75; Kuno et al. (1986) J. Biol. Chem. 261:5817–5823 (copurification from rat lung of ANP binding and guanylate cyclase activity). Of additional interest regarding the ANP receptor are Leitman et al. (1986) J. Biol. Chem. 261:11650–11655; Scarborough et al. (1986) J. Biol. Chem. 261:12960–12964; Hayashi et al. (1986) Peptide Chemistry 1985. pp. 27–32; Hirata et al. (1985) Biochem. Biophys. Res. Comm. 132:971–984; Napier et al. (1986) Arch. Biochem. Biophys. 248:516–522.

It would be highly desirable, therefore, if purified ANP receptor protein were available, as well as genes to facilitate its production through recombinant means. Monoclonal antibodies to the receptor protein would also be useful since they could be used to characterize the receptor protein, identify additional tissue expressing receptor protein, and block ANP binding to the receptor.

Several receptor molecules unrelated to the ANP receptor have been isolated and purified in the prior art. Wimalasena et al., (1985) J. Biol. Chem. 260:10689–10697 (porcine LH/hCG receptor); Petruzzelli et al., (1984) Proc. Natl. Acad. Sci. USA 81:3327–3331 (insulin receptor); Schneider et al., (1982) J. Biol. Chem. 257:2664–2673 (LDL receptor).

SUMMARY OF THE INVENTION

It is an object of the present invention to provide purified ANP receptor protein, both native and synthetic.

Another object of the present invention is to provide a method of purifying native ANP receptor protein.

Still another object of the present invention is to provide DNA molecules encoding ANP receptor protein.

Yet another object of the present invention is to provide methods of producing ANP receptor protein by recombinant DNA methods.

A further object of the present invention is to provide antibodies, and cell lines producing such antibodies, which bind an epitope on ANP receptor protein.

These and other objects of the present invention are provided by one or more of the following embodiments.

In one embodiment, the present invention is directed to a cell-free composition comprising mammalian Atrial Natriuretic Peptide (ANP) receptor protein subunit having a molecular weight of about 60.500 daltons, said receptor protein subunit comprising a minimum of about 75% by weight of the protein in said composition.

In another embodiment, the present invention is directed to proteins having substantial homology to the 60.5 kd ANP receptor subunit and which bind ANP.

In yet another embodiment, the present invention is directed to a method of purifying native ANP receptor protein comprising:

(i) providing a membrane-containing cell fraction prepared from mammalian cells having ANP receptors;

(ii) solubilizing ANP receptor protein in said membrane fraction with $C_{12}E_8$ detergent to produce a supernatant containing said ANP receptor protein; and (iii) purifying ANP receptor protein from said supernatant by passing said supernatant through a chromatographic column containing immobilized ANP under conditions whereby said ANP receptor protein is bound to said immobilized ANP, followed by eluting bound ANP receptor protein from said column to provide purified ANP receptor protein.

The present invention is also embodied in a method of isolating DNA sequences encoding ANP receptor protein comprising:

(i) providing a DNA library prepared from a mammalian cell source;

(ii) screening said DNA library by hybridization with a cDNA or oligonucleotide probe containing codons for an amino acid sequence homologous to a selected region of an ANP receptor protein subunit; and (iii) isolating DNA molecules from said DNA library to which said oligonucleotide selectively hybridizes.

Another embodiment of the present invention is a composition comprising a recombinant vector containing a DNA sequence encoding an amino acid sequence homologous to the 60.5 kd ANP receptor protein subunit, said composition being substantially free of recombinant vectors that do not contain said DNA sequence.

Other embodiments of the present invention are directed to cells, such as procaryotic and eucaryotic cells, which are transformed by the above vectors or DNA sequences, as well as methods of producing ANP receptor subunit comprising growing such cells under conditions whereby a peptide comprising ANP receptor protein subunit is expressed and recovered.

A further embodiment of the present invention is directed to anti-ANP receptor protein antibodies substantially free of other antibodies, immortal mammalian cells lines producing such antibodies, and methods of purifying ANP receptor protein with such antibodies.

BRIEF DESCRIPTION OF THE FIGURES

FIG. 2A shows the N-terminal amino acid sequence determined from purified bovine ANP receptor, and the corresponding synthetic oligonucleotides used to probe cDNA libraries.

FIGS. 3A, 3B, 3C and 3D is the bovine ANP receptor cDNA sequence and the predicted amino acid sequence.

FIGS. 5A, 5B, 5C, 5D, 5E and 5F are the human ANP receptor cDNA sequence and the predicted amino acid sequence.

DETAILED DESCRIPTION OF THE INVENTION

The present invention provides purified ANP receptor protein in a usable form. Purified ANP receptor protein allows for the amino acid sequence to be determined, nucleic acid probes designed, and ANP receptor genes cloned. See generally Atlas et al., supra; Yamanaka et al., supra; Maki et al., supra; Oikawa et al., supra. Once cloned, the ANP receptor gene can be used to produce synthetic ANP receptor protein. See, e.g., U.S. Pat. Nos. 4,440,859; 4,436,815; 4,431,740.

The receptor protein (native or synthetic) can be employed, for example, in competitive binding assays to measure the level of ANP in patient sera. ANP receptor protein will also be extremely useful in testing analogs to native ANP for their ability to bind or block the ANP receptor. Computer modeling of the ANP receptor binding site may also aid in the design of new compounds which block or bind the ANP receptor site in vivo.

"Atrial natriuretic peptide receptor protein", or "ANP receptor", refers to a native ANP receptor protein from any mammalian source, including, but not limited to, human, bovine, porcine, equine, ovine, murine, rat, rabbit, hamster, and goat. The term also includes synthetic ANP receptor protein; i.e., protein produced by recombinant means or direct chemical synthesis. See, e.g., Clark-Lewis et al (1986) *Science* 231:134–139. ANP receptor protein is a protein found in the cellular membrane of various vascular and renal tissues, including, but not limited to, kidney cortex cells, vascular endothelial cells, adrenal cortex, adrenal zona glomerulosa, and lung tissue.

The preferred receptor protein of the present invention is derived from vascular tissue, such as aortic smooth muscle cells. An illustrative member of the class of vascular ANP receptor proteins is the receptor protein isolated from bovine aortic smooth muscle cells (bovine vascular ANP receptor). ANP receptor protein of this class isolated from other tissues have the same structure. Bovine vascular ANP receptor protein is comprised of two substantially identical protein subunits. Analysis by sodium dodecylsulfate polyacrylamide gel electrophoresis (SDS-PAGE), 10% polyacrylamide concentration, shows that the dimer has an apparent molecular weight of 125±12 kd (non-reducing conditions) and that the subunit has an apparent molecular weight of 60.5±6 kd (reducing conditions).

Figure 1:
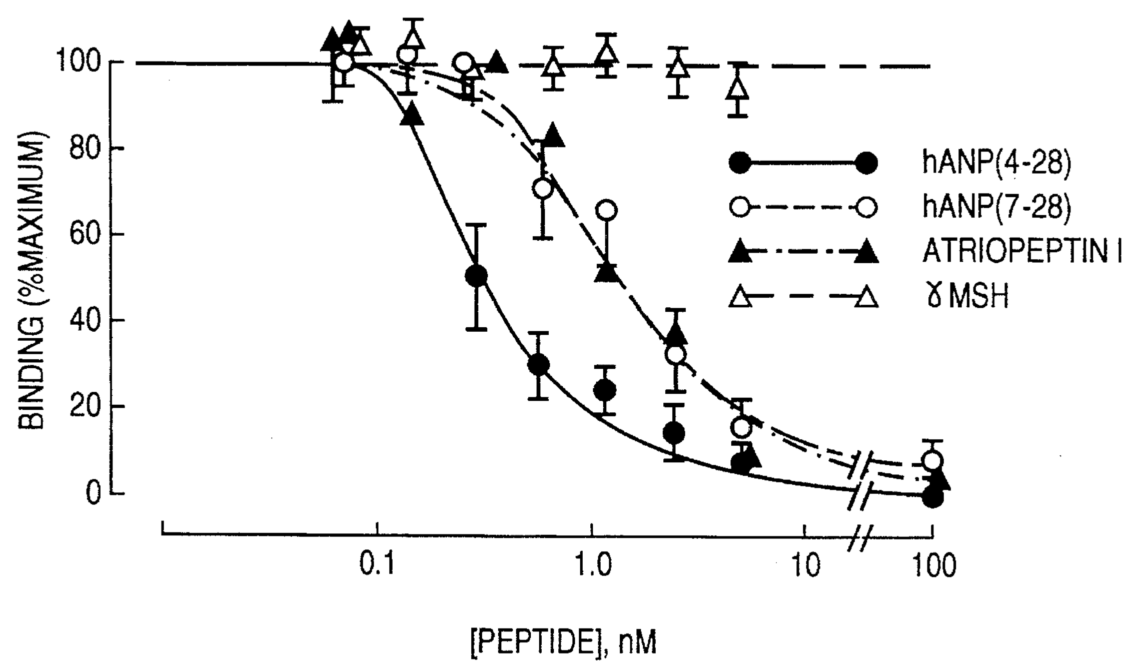
FIG. 1 shows the competitive binding between radiolabeled ANP(4-28) and various ANP peptides to purified ANP receptor protein.

To characterize the purified native bovine vascular ANP receptor protein further, its activity as a receptor in vitro was studied. The following ANP peptides, described in Schenk et al. (II), supra, were employed; ANP(4-28), ANP(7-28), and ANP(5-25). $B_{max}$, $K_i$ and $K_d$ were calculated by standard methods. See, e.g., Scatchard (1949) Ann. N.Y. Acad. Sci., pp. 600–672. Competitive binding analysis of ANP(4-28) with various ANP peptides is shown in FIG. 1. Computer analysis of the binding data shows that the $B_{max}$ for receptor binding is 5.7 (75% receptor activity) nmol/mg protein with a $K_d$ equal to 0.3 nM. This corresponds to a stoichiometry of ANP to receptor protein of 1:3/subunit, or 0.7:1/holoreceptor. Purified receptor protein also exhibited an affinity for ANP in the same range as previously recorded for ANP receptor in intact cells; 0.1–10.0 nM. The relative $K_i$ values for various ANP peptides are as follows; ANP(4-28) 0.3 nM; ANP(7–28) 1.1 nM; and ANP(5–25) 1.12 nM.

Native bovine vascular ANP receptor protein was also subjected to amino acid analysis. A partial N-terminal amino acid sequence of the bovine vascular receptor gave the following sequence for amino acids 2–32 of the mature protein;

```
              5                  10                  15
X—Ala—Leu—Pro—Pro—Gln—Lys—Ile—Glu—Val—Leu—Val—Leu—Leu—Pro—

              20                 25
Gln—Asp—Asp—Ser—Tyr—Leu—Phe—Ser—Leu—Ala—Arg—Val—Arg—Pro—

30
Ala—Ile—Glu—
```

One of skill in the art can readily extend the above sequencing to the carboxy terminus of the protein, if desired, by standard protein sequencing methods. A simpler method is to clone and sequence the gene for the receptor protein to give the amino acid sequence.

Analysis of the complete cDNA of the bovine receptor in FIG. 3 indicates that mature receptor protein is a 496 amino acid polypeptide, expressed as a propeptide. The molecular weight of the putative mature receptor protein is about 56,000, indicating that the native receptor protein may be glycosylated. The human cDNA (FIG. 5) shows a similar structure.

The prosequence of bovine vascular ANP receptor suggests that 41 amino acids are removed from the N-terminus of the receptor precursor during maturation. The first N-terminal 21 amino acids define an extremely hydrophobic potential membrane translocation signal. Walter et al. (1984) Cell 38:5–8. By the consensus rules of Von Heijne, (1983) Em. J. Biochem. 133:17–21, two highly probable sites for cleavage by signal peptidase occur in the predicted sequence, one after residue 18 and the other after residue 31. The remaining 10 to 23 residues between these sites and the mature N-terminus ($Glu^{42}$) suggest that subsequent proteolytic precessing of the receptor occurs either during transport to the membrane or after deposition. In this regard it is worth noting that the sequence preceding $Glu^{42}$ (residues 22–41) is hydrophilic and ends in a hexapeptide containing four arginines. Three potential carbohydrate addition sites are present; Asn 82, 289, and 465. The presence of $Cys^{496}$ so close to the transmembrane domain indicates that it is a likely site for the disulfide linkage of the homodimer.

Figure 4:
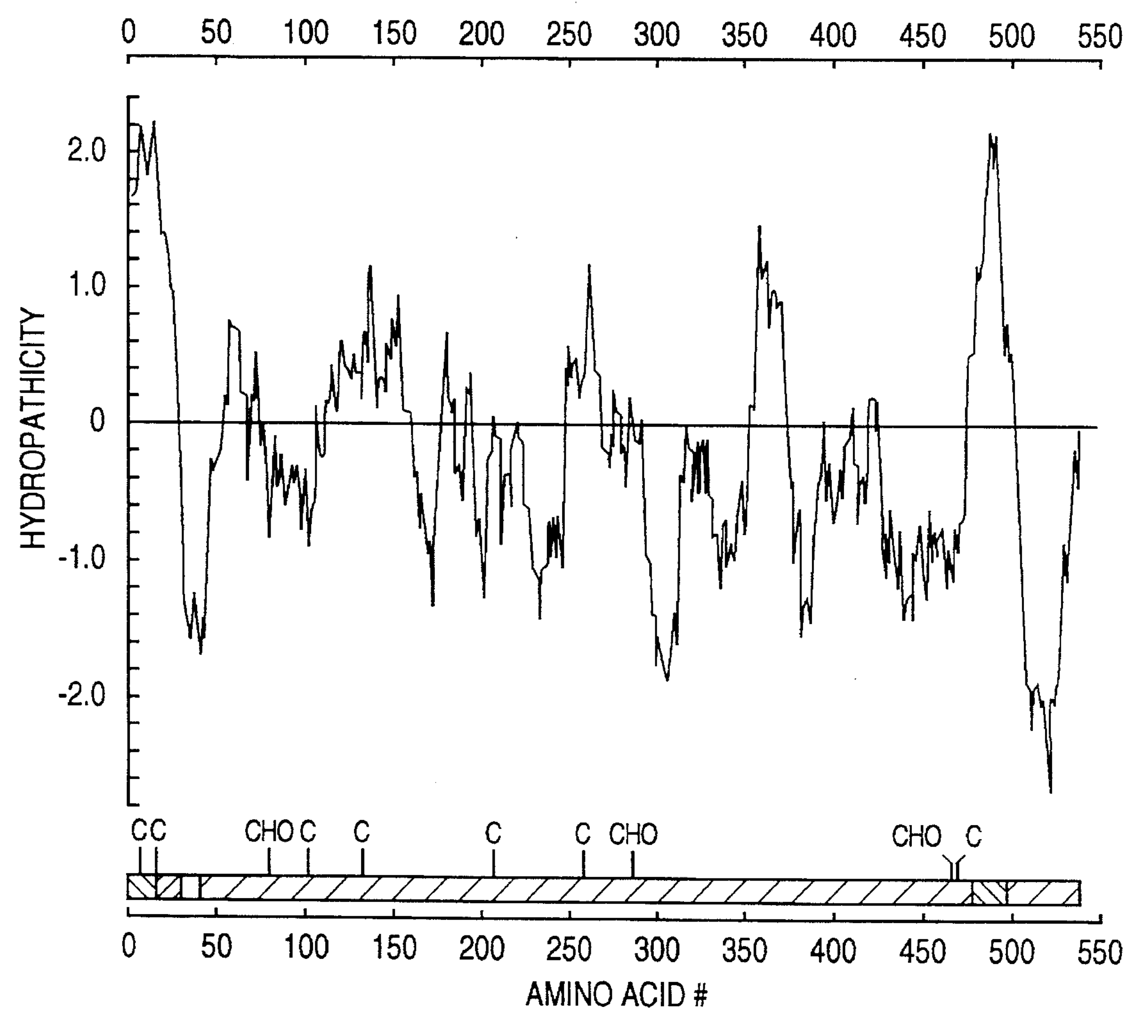
FIG. 4 is a hydropathicity profile of bovine ANP receptor protein.

The bovine vascular ANP receptor precursor contains several regions of significant hydrophobic character which are obvious from the hydropathicity plot of FIG. 4. At most, six hydrophobic regions of greater than 20 amino acids can be found, and the first of these (AA 1–21) is probably a signal peptide. One other extremely hydrophobic region (478–500) occurs adjacent to two very hydrophilic regions and is a likely candidate for a transmembrane domain. The region C-terminal to this domain begins with the sequence Arg-Lys-Lys-Tyr-Arg, which is an excellent potential membrane anchor. The ANP receptor is an acidic molecule with most of its negative charge outside the cell, possibly reflecting the fact that its ligand is a basic protein.

Further analysis of the content of particular amino acid residues in the native bovine receptor gave the results shown in Table I, where the results are expressed as number of amino acid residues (±20%) per 500 residues (estimate of 500 residues per 60 kd subunit).

TABLE I

| Amino Acid | No. of Residues* | |
|---|---|---|
| Aspartic Acid (Asp + Asn) | 27.0 | 14.0** |
| Glutamic Acid (Glu + Gln) | 21.3 | 36.8 |
| Serine (Ser) | 32.1 | 37.4 |
| Glycine (Gly) | 47.5 | 47.2 |
| Histidine (His) | 10.3 | 13.2 |
| Arginine (Arg) | 38.7 | 35.1 |
| Threonine (Thr) | 26.2 | 24.4 |
| Alanine (Ala) | 51.0 | 48.0 |
| Proline (Pro) | 25.2 | 22.1 |
| Tyrosine (Tyr) | 21.0 | 25.0 |
| Valine (Val) | 37.7 | 37.4 |
| Methionine (Met) | 8.6 | 6.6 |
| Isoleucine (Ile) | 32.5 | 27.2 |
| Leucine (Leu) | 48.7 | 54.6 |
| Phenylalanine (Phe) | 25.0 | 30.0 |
| Lysine (Lys) | 34.6 | 36.2 |
| Cysteine (Cys) | 2.0 | 4.6 |

*Est. of residues (±20%) in bovine vascular ANP receptor protein subunit per 500 residues.
**As before, but protein reduced and alkylated.

The amino acid composition of the purified receptor indicates that it contains 4.6 cysteine residues per 500 amino acids, which is in good agreement with the 5 predicted to be present in the mature receptor. The odd number of cysteines would appear to reflect the intermolecular disulfide bonds which hold receptor subunits together.

The above data indicate that the two subunits making up the native receptor are either identical or substantially identical (i.e., 90%–95% homologous). It is most likely that they are identical, which can be determined by further sequencing of the native peptide. cDNA or genomic clones.

The above data indicate that the ANP receptor described herein is a homodimer, the native subunit having a molecular weight of approximately 60,500, while the nonglycosylated subunit has a molecular weight of approximately 56,000. Some evidence indicates that there may also be native ANP binding proteins having molecular weights of approximately 120.000 and 70.000, and that there may be different functions for each of these proteins. For example, the 120 kd polypeptide observed under fully reducing conditions most closely correlates with guanylate cyclase activity. Unlike the 60.5 kd polypeptide described herein, it does not bind well to truncated ANP analogs. This suggests that the 120 kd receptor may be responsible for stimulating guanylate cyclase activity, while the 60.5 kd receptor has an alternative mode of action; e.g., a clearance receptor. Applicants, however, do not wish to be bound by this hypothesis. Despite the difference in molecular weight and activity, it may be that all of the observed species of ANP receptor protein are encoded by the same gene or a family of substantially similar genes and the observed differences could result from different post-transcriptional or post-translational processing.

The amino acid sequence of mammalian 60.5 kd vascular ANP receptor protein subunit is highly conserved among mammalian species and different tissues. For example, the bovine and human sequences are at least about 95–97% homologous, the human sequence being determined from kidney and placental cDNA. In general, native ANP receptor protein subunit (or the binding regions of related proteins) isolated from other species and/or tissues will have at least about 75% amino acid homology to bovine or human vascular ANP receptor protein subunit, and generally at least about 85% homology. In some cases, homology may be about 90% to about 95% or higher. Other native ANP receptor proteins will be comprised, therefore, of homologous protein subunits. These other solubilized ANP receptor proteins can be further characterized by their ability to bind ANP peptides with high affinity. For example, ANP(4-28) will have a $K_i$ value of ≦10–20 nM, and preferably ≦5 nM. It is particularly preferred that the ANP receptor protein have a relative $K_i$ value of≦ 1 nM for ANP(4-28).

Synthetic ANP receptor may also be slightly different from bovine or human vascular ANP receptor in amino acid composition. It is often expedient, for example, to change or delete amino acid residues in nonessential regions (i.e., that do not eliminate receptor function) when engineering an expression vector. It may also be desirable to deliberately alter the amino acid sequence to change the binding affinity to ANP. In general, the affinity ($K_i$) of synthetic receptor should be ≦10 nM for ANP(4-28). The amino acid sequence homology of synthetic receptor to bovine or human vascular ANP receptor will generally be in the range described above for native ANP receptors, at least for those regions that are not deleted or changed (e.g., as in a fusion protein).

Purification of ANP receptor protein from cells comprises three basic steps; preparation of the cells, solubilization of ANP receptor in an active and stable form, and purification of the receptor by affinity chromatography. A preferred cell source is bovine aortic smooth muscle cells, since they contain about 250,000 ANP receptor sites per cell. Cultured cells have the additional benefit of being relatively protease-free compared to most tissue sources. This facilitates stabilization and purification of active receptor protein. Other cell lines, such as the rat smooth muscle embryonic thoracic aortic cell line AlO (ATCC CRL-1476) are Known in the art.

The preferred cell line is established from explants of bovine aorta, as described by Longenecker et al., (1982) J. Cell Physiol. 113:197–202. The smooth muscle cell line can be grown in roller bottles by standard procedures and harvested when sufficient cell mass is obtained. Harvested cells are pelleted by centrifugation and then homogenized, for example, by grinding with a mortar and pestle. Receptor protein is then solubilized from this homogenized cell fraction with the detergent $C_{12}E_8$ (octaethyleneglycol dodecyl ether), available from Calbiochem-Behring (San Diego, Calif.). Numerous detergents were tried as a substitute for $C_{12}E_8$. None of the other detergents, however, solubilized the receptor protein without substantially reducing ANP receptor activity.

Solubilized ANP receptor is purified by affinity chromatography. Various methods of purification by affinity chromatography are known to those skilled in the art. See generally Cooper in TOOLS OF BIOCHEMISTRY, pp. 234–254 (John Wiley & Sons, 1977). The general approach for the purification of ANP receptor protein is; (1) passing the solubilized receptor fraction through a column to which an ANP peptide has been bound, (2) washing the column under dissociating conditions where the receptor remains bound to the ANP peptide, (3) dissociating the receptor/ANP complex, and (4) removing excess ligand and restoring binding activity of the receptor.

The above procedure provides a purified, cell-free composition wherein vascular ANP receptor protein comprises at least about 75–80% of the protein fraction of the composition. Preferably, chromatography conditions are selected so that the protein fraction of the composition comprises at least about 90% ANP receptor protein, and optimally at least about 98% receptor protein. By selection of cell source, various ANP receptor proteins, such as bovine or human, can be prepared. See generally ANIMAL CELL CULTURE (R. I. Freshney ed. 1986).

Once purified receptor protein is obtained, it can be readily sequenced by any of the various methods known to those skilled in the art. For example, the amino acid sequence of the receptor protein can be determined from the purified protein by repetitive cycles of Edman degradation, followed by amino analysis by HPLC. Other methods of amino acid sequencing are also known in the art.

Once the amino acid sequence is determined, oligonucleotide probes which contain the codons for a portion of the determined amino acid sequence are prepared and used to screen DNA libraries for genes encoding the receptor protein. The basic strategies for preparing oligonucleotide probes and DNA libraries, as well as their screening by nucleic acid hybridization, are well known to those of ordinary skill in the art. See, e.g., DNA CLONING: VOLUME I (D. M. Glover ed. 1985); NUCLEIC ACID HYBRIDIZATION (B. D. Hames and S. J. Higgins eds. 1985); OLIGONUCLEOTIDE SYNTHESIS (M. J. Gate ed. 1984); T. Maniatis, E. F. Frisch & J. Sambrook, MOLECULAR CLONING: A LABORATORY MANUAL (1982).

First, a DNA library is prepared. The library can consist of a genomic DNA library from a selected mammal, such as a human, Human genomic libraries are known in the art. See, e.g., Lawn et al., (1978) Cell 15:1157–1174. DNA libraries can also be constructed of cDNA prepared from a poly-A RNA (mRNA) fraction by reverse transcription. See, e.g., U.S. Pat. Nos. 4,446,235; 4,440,859; 4,433,140; 4,431,740; 4,370,417; 4,363,877. The mRNA is isolated from a cell line or tissue known to express the receptor protein. Cell lines or tissue expressing ANP receptor protein are known in the art, cDNA (or genomic DNA) is cloned into a vector suitable for construction of a library. A preferred vector is a bacteriophage vector, such as phage λ. The construction of an appropriate library is within the skill of the art.

Once the library is constructed, oligonucleotides to probe the library are prepared and used to isolate the desired ANP receptor protein gene. The oligonucleotides are synthesized by any appropriate method. The particular nucleotide sequences selected are chosen so as to correspond to the codons encoding a known amino acid sequence from the receptor protein. Since the genetic code is redundant, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. It may not be necessary, however, to prepare probes containing codons that are rare in the mammal from which the library was prepared. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the receptor protein. Probes covering the complete gene, or a substantial part of the genome, may also be appropriate, depending upon the expected degree of homology. Such would be the case, for example, if a cDNA of bovine vascular ANP receptor was used to screen a human gene library for human ANP receptor protein. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See generally, NUCLEIC ACID HYBRIDIZATION, supra. The basic requirement is that hybridization conditions be of sufficient stringency so that selective hybridization occurs; i.e., hybridization is due to a sufficient degree of nucleic acid homology (e.g., at least about 70–75%), as opposed to nonspecific binding. Once a clone from the screened library has been identified by positive hybridization, it can be confirmed by restriction enzyme analysis and DNA sequencing that the particular library insert contains a gene for the receptor protein.

Alternatively, a DNA coding sequence for ANP receptor subunit can be prepared synthetically from overlapping oligonucleotides whose sequence contains codons for the amino acid sequence of ANP receptor protein subunit. Such oligonucleotides are prepared by standard methods and assembled into a complete coding sequence. See, e.g., Edge, (41981) Nature 292:756; Nambair et al., (1984) Science 223:1299; Jay et al., (1984) J. Biol. Chem. 259:6311.

A DNA molecule containing the coding sequence for ANP receptor protein subunit can be cloned in any suitable vector and thereby maintained in a composition substantially free of vectors that do not contain the coding sequence of the ANP receptor gene (e.g., other library clones). Numerous cloning vectors are known to those of skill in the art, and the selection of an appropriate cloning vector is a matter of choice. Examples of recombinant DNA vectors for cloning and the host cells which they transform include bacteriophage λ (*E. coli*), pBR322 (*E. coli*), pACYC$_{177}$ (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtills*), pBD9 (Bacillus), pIJ61 (Streptomyces), pUC$_6$ (Streptomyces), actinophage ϕC31 (Streptomyces), YIp5 (yeast), YCp19 (yeast), and bovine papilloma virus (mammalian cells). See generally, DNA CLONING: VOLES I & II, supra; MOLECULAR CLONING: A LABORATORY MANUAL, supra.

In one embodiment of the present invention, the coding sequence from an ANP receptor protein gene is placed under the control of a promoter, ribosome binding site (for bacterial expression) and, optionally, an operator (collectively referred to herein as "control" sequences), so that the DNA sequence encoding the receptor protein (referred to herein as the "coding" sequence) is transcribed into RNA in the host cell transformed by the vector. The coding sequence may or may not contain a signal peptide or leader sequence. The coding sequence may also contain either the sequence for pro ANP receptor, or for mature ANP receptor. In bacteria, mature receptor protein subunit is preferably produced by the expression of a coding sequence which does not have any signal peptide, or by expression of a coding sequence containing the leader sequence in a system when post-translational processing removes the leader sequence. The determination of the point at which the mature protein begins and the signal peptide ends is easily determined from the N-terminal amino acid sequence of the mature protein (FIG. 2). The receptor protein can also be expressed in the form of a fusion protein, wherein a heterologous amino acid sequence is expressed at the N-terminal. See, e.g. U.S. Pat. Nos. 4,431,739; 4,425,437.

The recombinant vector is constructed so that the receptor protein coding sequence is located in the vector with the appropriate control sequences, the positioning and orientation of the receptor coding sequence with respect to the control sequences being such that the coding sequence is transcribed under the control of the control sequences (i.e., by RNA polymerase which attaches to the DNA molecule at the control sequences). The control sequences may be ligated to the coding sequence prior to insertion into a vector, such as the cloning vectors described above. Alternatively, the coding sequence can be cloned directly into an expression vector which already contains the control sequence and an appropriate restriction site downstream from control sequences. For expression of the receptor protein coding sequence in procaryotes and yeast, the control sequences will be heterologous to the coding sequence. If the host cell is a procaryote, it is also necessary that the coding sequence be free of introns; e.g., cDNA. If the selected host cell is a mammalian cell, the control sequences can be heterologous or homologous to the receptor protein coding sequence, and the coding sequence can be genomic DNA containing introns or cDNA. Either genomic or cDNA coding sequence may be expressed in yeast.

A number of procaryotic expression vectors are known in the art. See, e.g., U.S. Pat. Nos. 4,440,859; 4,436,815; 4,431,740; 4,4310739; 4,428,941; 4,425,437; 4,418,149; 4,411,994; 4,366,246; 4,342,832. See also British Patent Specifications GB 2,121,054; GB 2,008,123; GB 2,007,675; and European Patent Specification 103,395. Preferred expression vectors, however, are those for use in eucaryotic systems. Yeast expression vectors are known in the art. See, e.g., U.S. Pat. Nos. 4,446,235; 4,443,539; 4,430,428. See also European Patent Specifications 103,409; 100,561; 96,491. Another preferred expression system is vector pHS1, which transforms the Chinese hamster ovary cells.

Recombinant ANP receptor protein subunit can be produced by growing host cells transformed by the expression vector described above under conditions whereby the ANP receptor protein is produced. ANP receptor protein is then isolated from the host cells and purified. If the expression system secretes ANP receptor protein into growth media, the receptor protein can be purified directly from cell-free media. To obtain secretion, it will generally be necessary to delete the codons for the membrane binding portion of the receptor. If the receptor protein is not secreted, it is isolated from cell lysates. The selection of the appropriate growth conditions and recovery methods are within the skill of the art.

Either native or synthetic ANP receptor protein can be used to produce antibodies, both polyclonal and monoclonal. If polyclonal antibodies are desired. purified receptor protein is used to immunize a selected mammal (e.g., mouse, rabbit, goat, horse, etc.) and serum from the immunized animal later collected and treated according to known procedures. Compositions containing polyclonal antibodies to a variety of antigens in addition to the receptor protein can be made substantially free of antibodies which are not anti-ANP receptor protein antibodies by passing the composition through a column to which ANP receptor has been bound. After washing, polyclonal antibodies to ANP receptor are eluted from the column. Monoclonal anti-ANP receptor protein antibodies can also be readily produced by one skilled in the art. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Bart virus. See, e.g., M. Schreier et al., HYBRIDOMA TECHNIQUES (1980); Hammerling et al., MONOCLONAL ANTIBODIES AND T-CELL HYBRIDOMAS (1981); Kennett et al., MONOCLONAL ANTIBODIES (1980).

By employing ANP receptor protein (native or synthetic) as an antigen in the immunization of the source of the B-cells immortalized for the production of monoclonal antibodies, a panel of monoclonal antibodies recognizing epitopes at different sites on the receptor protein molecule can be obtained. Antibodies which recognize an epitope in the binding region of the receptor protein can be readily identified in competition assays between antibodies and ANPs. Such antibodies could have therapeutic potential if they are able to block the binding of ANP to its receptor in vivo without stimulating the physiological response associated with ANP peptide binding. Antibodies which recognize a site on the receptor protein are also useful, for example, in the purification of ANP receptor protein from cell lysates or fermentation media, and in characterization of the receptor protein. In general, as is known in the art, the anti-ANP receptor antibody is fixed (immobilized) to a solid support, such as a column or latex beads, contacted with a solution containing the receptor protein, and separated from the solution. The receptor protein, bound to the immobilized antibodies, is then eluted.

The following examples are presented for illustrative purposes only and are not intended to limit the scope of the invention in any way.

Example I

This example is directed to the purification of ANP receptor protein from vascular tissue and its physical characterization.

The bovine aortic smooth muscle (BASM) cell line was originally established by Longenecker et al. and is described at (1982) J. Cell Physiol. 113:197–202. A bovine aortic smooth muscle cell line established according to this method and named Q-2 has been deposited with the American Type Culture Collection (ATCC), 12301 Parklawn Drive, Rockville, Md., U.S.A. under the accession number CRL-9088. After initial growth in tissue culture and subsequent cloning, stockpiles of cells were frozen in liquid nitrogen. Cells used for purification of the ANP receptor protein were obtained after 4–15 passages of the cells. The cells were grown under standard conditions in 15% bovine serum and Dulbecco's Modified Eagle's medium in 100 roller bottles (850 $cm^2$ each). Cells were harvested from the roller bottles by twice rinsing with 50 ml of phosphate-buffered saline (PBS) containing 5 mM EDTA. The same buffer containing 10 μg/ml elastase and 25 μg/ml collagenase was then added to each roller bottle. After an 8–10 min incubation with constant rolling, released cells were pooled, placed on ice, and bovine serum added to 5% (v/v). The cells were centrifuged at 5,000×g for 10 min at 4° C. The pellet was resuspended in 250 ml of PBS/EDTA and centrifuged in the same manner. This pellet was again resuspended in 30 ml of homogenization buffer (50 mM Tris HCl. pH 7.5; 5 mM EDTA; 100 mM NaCl; 0.25M sucrose; 0.1 mM phenyl methyl sulfonyl fluoride; 25 μg/ml aprotinin; 25 μg/ml leupeptin) at 4° C.

The cells were homogenized using 10 strokes with a ground glass pestle in a mortar placed on ice. The homogenized cells were centrifuged at 100,000×g for 30 min at 4° C. The pellet was resuspended in homogenization buffer and re-homogenized as described above. This material was again centrifuged at 100,000×g for 30 min at 4° C. The final pellet was resuspended in 10 ml of homogenization buffer, and protein content was determined by the method of Bradford. (1976) Anal. Biochem. 7.2:248–251. The membranes were adjusted to 5 mg protein/ml by the addition of homogenization buffer. Receptor binding activity in this fraction was detected with $^{125}$I-ANP(2–28) as described in Schenk et al., (1985) Biochem. Biophys. Res. Commun. 127:433–442. The concentration-dependent binding exhibited by this fraction suggested that 80% of the cell surface receptor activity remained at this stage of the purification.

The membrane fraction exhibiting ANP receptor activity was diluted in an equal volume of PBS/EDTA, followed by the slow addition over a 10-min period of a solution containing $C_{12}E_8$ detergent (20 mg/ml) until a final $C_{12}E_8$ concentration of 4 mg/ml was obtained. This solution was then centrifuged at 100,000×g for 1 hr at 4° C. and the supernatant retained. Binding studies, as described above, showed that 65% of the total ANP binding sites in the membranes were solubilized by this procedure. The solubilized ANP receptor from this preparation was extremely stable, and no change in binding activity was detected after storage of two weeks at 4° C. or three months at −20° C.

An affinity matrix was made by coupling 40 mg human ANP(4-28) to 4 ml of Affi-gel 10 (Bio-Rad) as described by the manufacturer. Solubilized ANP receptor was adjusted to 10 mM $CaCl_2$ and $MgCl_2$ and filtered through 0.2 μM filters (type GE, Millipore). The filtrate was chromatographed on the ANP-agarose column at a flow rate of 0.5 ml/min at 21° C. The column was washed with binding buffer (100 mM Tris HCl, pH 7.50; 100 mM NaCl; 4 mg/ml $C_{12}E_8$; 10 mM $CaCl_2$; and 10 mM $MgCl_2$) until the effluent reached $A_{280}$= 0.000. Then 6.0 ml of elution buffer (10 mM Na acetate, pH 5.00:100 mM NaCl; 4 mg/ml $C_{12}E_8$; 10 mM $CaCl_2$; 10 mM $MgCl_2$) was added and the eluent was placed on ice and immediately adjusted to 37% (v/v) acetone. The solution was centrifuged at 4,000×g for 10 min at 4° C. and thoroughly aspirated. The pellet was resuspended in 3.0 ml of binding buffer and analyzed for purity, receptor binding activity, and amino acid sequence.

Analysis by SDS-PAGE (10% polyacrylamide concentration) under reducing and non-reducing conditions was conducted. Under non-reducing conditions, a single protein band at 125 kd was seen. Treatment of the purified receptor with 10 mM dithiothreitol, a reagent that reduces cystine residues to cysteines, resulted in the appearance of a single protein band at 60.5 kd. This data demonstrates that the ANP receptor protein is essentially pure, and that the active receptor from aortic smooth muscle cells is a dimer of two identical subunits attached by disulfide bridges.

Competitive binding of $^{125}$I-ANP(4-28) against various ANP peptides to the purified receptor is shown in FIG. 1. The tested ANP peptide included hANP(4-28), hANP(7-28) and atriopeptin I. Gamma-melanocyte stimulating hormone (γ-MBH) was employed as a negative control. Computer analysis (program RS-1; Bolt, Beranek & Newman, Boston, Mass.) of the binding data showed that the $B_{max}$ for the receptor binding is 5.7 nmol/mg protein with a $K_d$=0.3 nM. This corresponds to a stoichiometry of ANP to receptor protein of 1:3 kd subunit, or 0.7:1.0/holoreceptor.

Additional studies were conducted with ANP peptides. The relative $K_i$ values of 0.3 nM for ANP(4-28), 1.1 nM for ANP(7-28), and 1.12 nM for ANP(5-25) are in agreement with data reported previously for cell surface receptors.

Twenty-five μg of the purified ANP receptor was subjected to repetitive cycles of Edman degradation, followed by amino acid analysis using HPLC on a Applied Biosystems 470A gas-phase sequnator. Analysis revealed only a single sequence of amino acids. This sequence, and corresponding nucleotide sequences, are shown in FIG. 2A.

Example II

This example is directed to a protocol for obtaining full-length coding sequences of the bovine ANP receptor.

Probes were designed based on the N-terminal sequence of ANP receptor deduced in Example I. The sequences are shown in FIG. 2A. Oligonucleotide sequences are presented 3' to 5'. Probes were (1) a 24-fold degenerate 14-mer probe, (2) a 48-fold degenerate 14-mer probe, and (3) a 51-mer probe designed using bovine preferred codon choices. Four different versions of probe 3 were prepared in case the AGA/G codon was used for serine instead of the TCX codon, and in case CpG, a dinucleotide under-represented in eukaryote genomes, was not present in the receptor mRNA. Accordingly, boxed nucleotides indicate that either A was present in both positions or G was present in both positions. Asterisks indicate mismatches in the 51-mer probe versus the receptor cDNA sequences obtained (see FIG. 2A). Hybridization probes were synthesized (Applied Biosystems model 380a), purified by gel electrophoresis, and radiolabeled with [$^{γ32}$P]ATP and T4 polynucleotide kinase.

A cDNA was prepared from BASM cells as follows. Membrane associated polysomes were purified from BASM cells essentially as described [Sebbain, R. et al. (1983) J. Biol. Chem. 258:3294–3303] and double-strand cDNA was synthesized by the method of Land et al. (1981) Nucleic Acids Res. 9:2251–2266. cDNAs fractionated on Sephacryl S400 (Pharmacia) were ligated to EcoRI adapters and cloned in kgt10 [Wood, et al. (1984) Nature 312:330–333]. A library of app. $9\times10^6$ recombinant phage was obtained. Plaque lifts were screened by hybridization with combined 51-mer probes in 20% formamide plus 6× SSC (0.9M NaCl, 0.09M sodium citrate), 10% dextran sulfate, 0.1% SDS, 5× Denhardt's (0.1% each of bovine serum albumin, polyvinyl pyrrolidone, and Ficoll), and 100 μg/ml yeast ribosomal RNA at an initial temperature of 55° C., dropping to 40° C. overnight. Clones corresponding to positive hybridization signals were confirmed by hybridization to probes 1 and 2 and plaque purified. Two clones (pANPRc-1 and pANPRc-2) were obtained from about 300,000 plaques. After partial sequence determination by the M13 method, Sanger et al. (1977) Proc. Natl. Acad. Sci. USA 74:5463–5469; Messing et al. (1982) Gene 19:269–276, additional probes (nondegenerate 20-mers) were prepared and used to obtain clones pANPRc-4, 12, 13, 14, and 15 from the same cDNA library. Probes based on the pANPRc-4 sequence were used to obtain pANPRc-6 and probes based on the pANPRc-6 sequence used to obtain pANPRc-9 and 10. The total frequency of ANP receptor clones in the cDNA library which were detected with various probes was about one per 20,000.

Figure 2B:
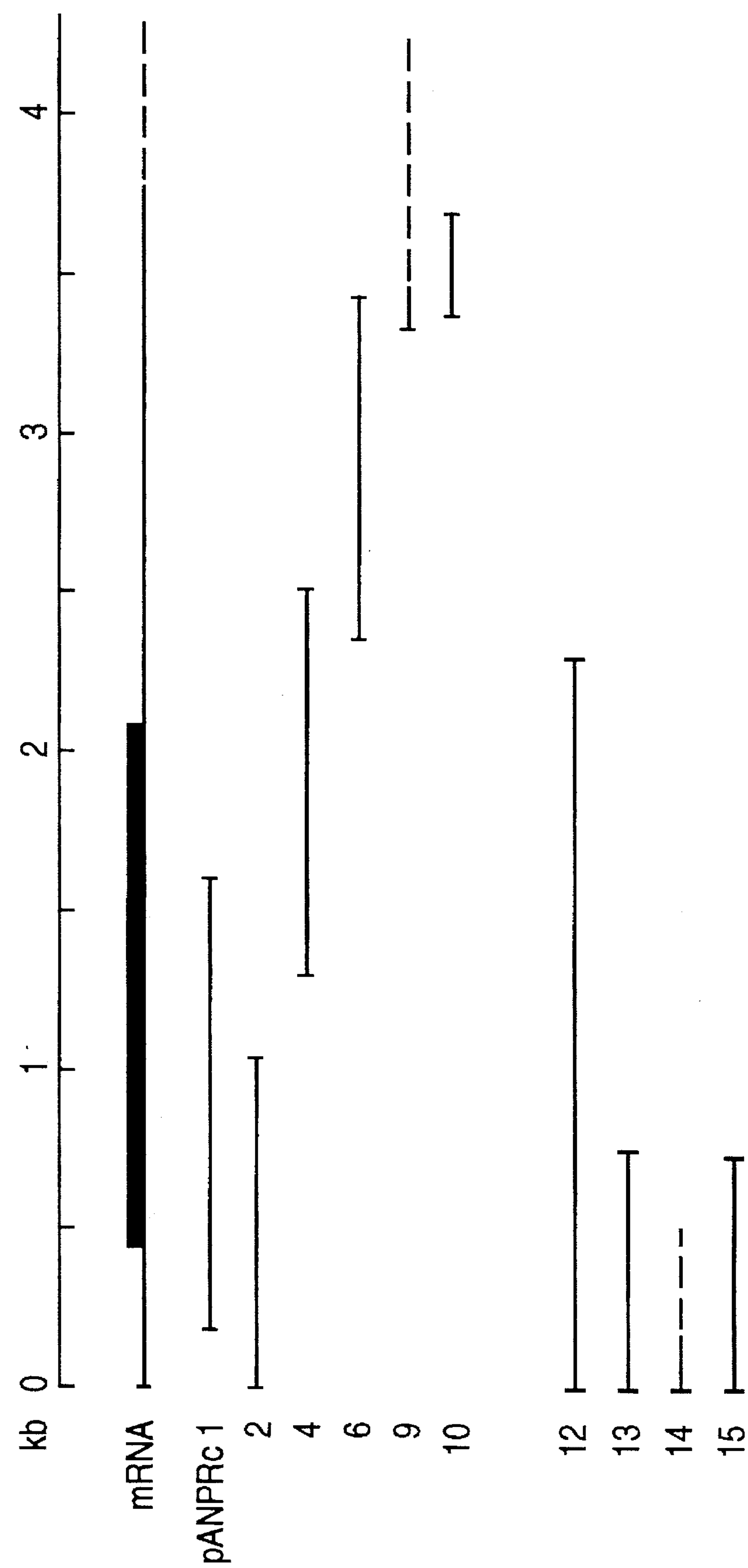
FIG. 2B is a schematic representation of the ANP receptor RNA and the cDNA clones obtained with the probes in FIG. 2A.

The ANP receptor cDNA clones are aligned by sequence in FIG. 2B. The coding segment (open reading frame) is indicated by the bold line, while the sequences from individual clones are indicated below. Dashed lines indicate regions where sequence analysis is incomplete. In total, they define over 3558 nucleotides of mRNA sequence. The open reading frame is 1611 nucleotides in length. This includes an in-frame segment encoding the N-terminal amino acid sequence of FIG. 2A. The sequences of the 5' ends of clones pANPRc-2, pANPRc-12 and pANPRc-15 are identical while those of pANPRc-13 and pANPRc-14 differ by 4 and 3 nucleotides, respectively. The 5' end of the ANP receptor mRNA thus appears to contain 465 noncoding nucleotides. Nearly 1500 nucleotides of 3' noncoding sequence have been obtained with over 500 more defined by partial sequence and mapping of pANPRc-9. None of the clones contain a poly(A) sequence indicative of an mRNA 3' terminus, although two potential poly(A) addition signals (AAUAAA) are present at 2440 and 3197 nucleotides. The receptor appears, therefore, to be encoded at the 5' end of a large (>4000 nucleotide) mRNA. This is similar to the mRNA structure of other receptors for polypeptides.

A clone containing the entire ANP Eeceptor coding region was constructed in pGEM1 (Promega Biotec) by combining pANPRc-1 and pANPRc-4 utilizing a NcoI restriction site common to both. The resultant clone, pANPRc-1/4, contains a 2290 base pair DNA insert which includes the entire open reading frame, 233 nucleotides of the 5' noncoding region and 190 nucleotides of 3' noncoding sequence. Restriction of the 3' plasmid/cDNA junction with EcoRI and subsequent transcription with SP6 polymerase resulted in a synthetic RNA of ~2300 nucleotides as determined by agarose gel electrophoresis.

The primary structure of the receptor was determined by analysis of the sequences of all the clones. The cDNA sequence and predicted amino acid sequence is shown in FIG. 3. The numbers on the right indicate the nucleotide position in the sequence. The predicted amino acid sequence of the preproreceptor is indicated below the codons of the uninterrupted coding region. Amino acid numbers beginning with MET (001) are indicated. Several single nucleotide differences between different clones were noted, four of these in the coding region. Nucleotides 552, 1010, 1436, and 1558 were G in pANPRc-2, C in pANPRc-1, and A in pANPRc-4, respectively. Since this frequency is similar to the error frequency associated With Reverse Transcriptase, Guidon et al. (1983) Meth. Enzymol. 101:370–386, it is likely that these differences are cloning artifacts. The sequence in FIG. 3 represents the consensus of at least 2 clones in each position. Potential signal peptidase cleavage sites (▲) and the beginning of the mature receptor N-terminus (↓) are shown. Potential N-linked glycosylation sites are boxed and the putative transmembrane domain is denoted by the bar. Potential poly(A) addition signals in the 3' noncoding region are overlined.

An open reading frame 538 codons defines the primary structure of the bovine ANP receptor. The ANP receptor precursor polypeptide is thus predicted to be composed of 537 amino acids with a molecular weight of 59,744 daltons. Although the ATG shown as the initiation codon in FIG. 3 is preceded by four additional ATGs which could be start codons, the latter four are followed by stop codons in each reading frame as well as by a T-rich region which would encode an unlikely oligophenylalanine stretch in any frame. A good translation initiation signal (GCACG) ad defined by Kozak ($CC^{A}/_{G}CC$), (1986) Cell 44:283–292, precedes the predicted ATG and this ATG is in frame with an oligopeptide sequence identical to the N-terminal sequence of the isolated receptor. The size predicted for the receptor precursor is in excellent agreement with the observed size of the in vitro translation product (Mr ~58.000) of RNA synthesized using the cDNAs as template, and the amino acid composition of the purified receptor is also in good agreement with the predicted sequence. Finally, characteristics of the sequence are consistent with known and presumed characteristics of the receptor.

The hydropathicity profile of the receptor amino acid sequence was also calculated by the method of Kyte and Doolittle. (1982) J. Mol. Biol. 157:105–132. Local hydropathicity values were averaged from residue x–9 to x+9 and plotted versus residue×(Amino Acid #) as shown in FIG. 4. Positive values indicate hydrophobic regions and negative calues indicate hydrophillic regions. A schematic representation of the receptor protein is depicted below for reference. Filled-in regions indicate the putative signal and transmembrane sequences respectively. The stippled region denotes the area within which signal peptidase presumably cleaves and the open region denotes additional amino acids removed during receptor maturation. References sequences in the receptor are cysteine (C) and the Asn-X-Ser/Thr potential glycosylation sites (CHO).

*E. coli* (pANPRc-1) was deposited on 5 May 1986 with the American Type Culture Collection. 12301 Parklawn Drive, Rockville, Md. 20852, U.S.A., under the terms of the Budapest Treaty on the Deposit of Microorganisms. The deposit has been assigned accession number 67105. To the extent of any discrepancies between the sequence shown in FIGS. 2A and 3, and the sequence contained in the deposited clone pANPRc-1, the latter is controlling.

Example III

The following example describes the cloning of a full-length human ANP receptor coding sequence.

To obtain a human ANP receptor clone. a human kidney cDNA library was screened using nick-translated coding sequence of the bovine clone (a 1.4 kb fragment; pANPR-1). Of approximately $1\times10^{6}$ members screened, 4 were positive. Three of these were independent overlapping clones of 1096 bp (clone 1-1-1), 925 bp (clone 12-1-2) and 813 bp (clone 16-1-1) having homology to the 1083 and 2121 bp region in the bovine clone. Relative to the bovine clone sequence, the clone 1-1-1 has a 3 bp deletion at 1873, and all three clones shown are identical 12 bp insertion in the 3' untranslated region. All three clones terminate at an EcoRI site and do not have a poly A tail.

Approximately $0.5\times10^{6}$ members of a human placental cDNA library, when screened with 2 28-mer oligonucleotides (1119–1147 bp and 1166–1194 bp in human sequence) and a nick-translated 243 bp EcoRI/SacI fragment from clone 1-1-1 ($pANPHRC_2$), gave one independent clone of 1636 bp (clone 4-2) having homology to the 96 to 1732 bp region in the bovine clone. This clone may have 12 bp insertion at 550 bp relative to the bovine clone.

$pANPHRC_4$, a human receptor clone having full-length coding sequence, is made by ligation of the ca 1250 bp EcoRI/SacI fragment from clone 4-2 (pANPHRC1) and the ca 700 bp SacI/EcoRI fragment from clone 12-1-2 (pANPHRC3) into the EcoRI-digested and CIP-treated vector $pUC_9$. FIG. 5 shows this human receptor clone sequence with 5' untranslated region, signal sequence, initiating Met, coding region, 3' untranslated region, and amino acid differences from the bovine.

*E. coli* (pANPHRC1) and *E. coli* (pANPHRC3) were deposited on 8 May 1987 with the American Type Culture Collection under the terms of the Budapest Treaty on the Deposit of Microorganisms. The deposits have been assigned accession numbers 67401 and 67402, respectively. To the extent of any discrepancy between the sequence shown in FIG. 5 and the sequence contained in these deposited clones, the latter are controlling.

Example IV

The following demonstrates that the ANP receptor described herein is found in a range of tissues known to exhibit ANP binding.

In order to determine whether the cloned sequence was expressed in tissues and cells known to display the ANP receptor. Northern blot analysis was performed. Cell lines were grown in Dulbecco's modified Eagle's medium containing 10% fetal calf serum with 10% $C)_2$ at 37° C. until confluent. Poly(A) RNAs were isolated by the guanidine isothiocyanate method. Chargwin, et al. (1979) Biochem. 18:5294–5299, followed by oligo(dT) cellulose chromatography. RNA was denatured in formamide and formaldehyde at 50° C. and then separated on a 1.4% agarose gel containing formaldehyde, and transferred to nitrocellulose. The filters were hybridized in 50% formamide plus 5× SSC to pANPRc-1 insert DNA made radioactive by nick translation. Filters were washed at 65° C. in 1× SSC plus 0.1% SDS and subjected to autoradiography.

Poly(A)-containing RNAs homologous to the cloned sequence are present as discrete species in three bovine primary cell lines which display ANP receptors; aortic endothelial cells (BAE), adrenal cortical cells (BAC), and the aortic smooth muscle cells (BABM) from which the cDNA clones were derived.

Since kidney and adrenal tissues also express ANP receptors, poly(A) RNAs isolated from these tissues were analyzed. Bovine kidney RNA was found to contain discrete RNA species homologous to the cloned sequence with fractionated papillae and cortex showing virtually identical patterns. These results are consistent with UV-photoaffinity labeling studies which show that the Mr ~60,000 ANP binding subunit is present in both glomerulus and inner medullary collecting duct regions of the kidney. The analysis was unable to detect receptor message in RNA from whole adrenal, however.

An additional result of the Northern analysis is that at least four discrete RNA species are present in the cultured cells. The major receptor RNA apparent in BAC and BAE cell RNAs is ~8000 nucleotides in length, but a ~3100 nucleotide RNA is also detected, and minor bands can be seen at ~4000 and ~5000 nucleotides. The 8000 nucleotide RNA is not an unspliced pre-mRNA since it is found in RNA fractionated to remove nuclear RNAs. The smaller RNAs are also not likely discrete degradation products since they contain both the 5' end and a poly(A) tail, as evidenced by the fact that they are detected equally with probes to 5= coding or 3' coding regions and were isolated by oligo(dT)-cellulose chromatography.

Heterogeneity of ANP receptor mRNAs could be the result of alternative splicing or transcription of different genes. Since the different species cannot be distinguished by increasing hybridization wash stringencies, they are not the product of relatively divergent genes. Also, given that only a single mRNA species (~5600 nucleotides) is detected in human tissues, receptor mRNA heterogeneity in the cow is of questionable functional significance. Length heterogeneity is frequently observed among receptor mRNAs, and may well be due to differences in lengths of 3' noncoding regions as has been shown for the IL-2 receptor mRNAs. The data above and the presence of two potential poly(A) addition signals in the 3' noncoding region of the ANP receptor clones suggest that length differences in ANP receptor mRNAs is due to differences in lengths of 3' noncoding regions.

Example V

The following example describes the expression of recombinant ANP receptor in a heterologous mammalian cell, as well as in vitro transcription of ANP receptor mRNA.

To demonstrate that pANPRc-1/4 actually encodes the ANP receptor, it was tested for its ability to elicit specific ANP binding in a heterologous system, *Xenopus oocytes*. The receptor coding sequence from pANPRc-1/4 was cloned into pGEM1 (ProMega, Madison, Wis.) and RNA prepared according to the supplier's instructions. Oocyte preparation and injection were performed essentially as described, Gurdon et al. (1983) Meth. Enzymol. 101:370–386. Typically, each oocyte was injected with 50 nl 50 ng synthetic RNA followed by incubation in modified Barth's saline at 21° C. for 48 hr. Crude membranes were prepared and solubilized in receptor binding buffer (2 mg/ml $C_{12}E_8$, 100 mM NaCl, 10 mM $MgCl_2$, 10 mM $CaCl_2$ and 100 mM Tris:HCl; pH 7.5). Binding was measured after incubating 0.5 ml of membrane suspension containing 10 μg protein with $2\times10^5$ cpm of [$^{125}$I] rAMP (1× $10^3$ cpm/fmol) and the indicated concentration of unlabeled ANP analog for 30 min at 21° C. Reactions were terminated and free peptide separated from bound by precipitation with acetone (40% v/v final). Counts bound in the absence of unlabeled ligand were 2048± 374 cpm while nonspecific binding (counts bound in the presence of 20 nM rANP) were 592±89 cpm. Bombesin (Peninsula Labs) has no effect on binding even at 100 μM.

Only low level, nonspecific binding was detected in membranes of uninfected, or mock injected eggs. However, saturable, specific binding of radiolabeled ANP was demonstrated in solubilized membranes of oocytes which had been injected with synthetic mRNA. Both rANP (4-28) and the truncated analog rANP (4-28) for binding. The $I_i$ apparent obtained from the experiment was 0.27 nM for both analogs. Binding was specific for ANP analogs since bombesin, an unrelated tetradecapeptide, did not compete for binding. In vitro transcription of the ANP receptor coding region of pANPRc-1/4 and subsequent translation in a cell free reticulocyte lysate demonstrated that the synthetic RNA was a functional mRNA encoding an Mr~ 58,000 polypeptide as judged by SDS-polyacrylamide gel electrophoresis.

Example VI

This example is directed to a protocol useful in the expression of coding sequences obtained according to Examples II, III or VIII.

cDNA clones encoding ANP receptor protein are most conveniently used to produce recombinant proteins in a variety of hosts, as described above. Expression in mammalian systems, however, is favored, as the host is capable of post-translational processing analogous to that experienced by natively produced protein. Thus, either cDNA or genomic sequences may be used.

A full-length cDNA (Example II or III) or genomic (Example VIII) ANP receptor-encoding clone is prepared for insertion into a host vector. The cloned insert is excised with EcoRI by partial digestion when the insert itself contains EcoRI sites. If necessary, other appropriate enzymes can be used, and the insert provided with EcoRI linkers. Then the excised insert is placed into the host vector pHS1, as described below.

The plasmid pHS1 is suitable for expression of inserted DNA in mammalian hosts. It contains 840 bp of the hMT-II sequence from p84H (Karin et al., (1982) Nature 299: 297–802) which spans from the HindlII site at position −765 of the hMT-II gene to the BamHI cleavage site at base +70. To construct pHS1, plasmid p84H was digested to completion with BamHI, treated with exonuclease BAL-31 to remove terminal nucleotides, and then digested with HindIII. The desired 840 bp fragment was ligated into pUC8 (Vieira et al., (1982) Gene 19: 259–268) which had been opened with HindIII and HincII digestion. The ligation mixture was used to transform *E. coli* HB101 to $Amp^R$, and one candidate plasmid designated pHS1, was isolated and sequenced by dideoxy sequencing. pHS1 contains the hMT-II control sequences upstream of a polylinker containing convenient restriction sites.

The ANP receptor subunit coding sequence, prepared as above, is ligated into EcoRI digested pHS1 and the ligation mixture used to transform *E. coli* MC1061 to $Amp^R$. Successful transformants are screened by restriction analysis, and a strain containing the desired plasmid, pMT-ANPr is further propagated to prepare quantities of plasmid DNA.

Chinese hamster ovary (CHO)-K1 cells are grown on medium composed of a 1:1 mixture of F12 medium and DME medium with 12% fetal calf serum. The competent cells are co-transformed with pMT-ANPr and pSV2:NEO (Southern et al., (1982) J. Mol. Appl. Genet. 1: 327–341). pSV2:NEO contains a functional gene conferring resistance to the neomycin analog G418. In the transformation, 500 ng of pSV2-NEO and 5 μg of pMT-ANPr are applied to a 16-mm dish of cells in a calcium phosphate-DNA coprecipitate according to the protocol of Wiglet et al., (1979) Cell 16: 777–785, with the inclusion of a two minute "shock" with 15% glycerol after four hours of exposure to the DNA. A day later, the cells are subjected to i mg/ml G418 to provide a pool of G418-resistant colonies, which are assayed for ANP receptor production and then cloned out.

Successful transformants, also having a stable inheritance of pMT-ANPr, are plated at low density for purification of clonal isolates. Small amounts of these isolates are grown in multi-well plates after exposure to $10^{-4}$M zinc chloride for convenient assay of ANP receptor production. ANP receptor determinations are made by standard ELISA or radioimmunoassays against antisera prepared against the appropriate ANP receptor protein using standard methods. Clonal isolates which produce large amounts of the desired ANP receptor are selected.

The cells, which are shown to produce ANP receptor under suitable conditions, are then seeded at 1/10 confluency in basal medium supplemented with 10% fetal calf serum, incubated overnight, and then induced for ANP receptor production by addition of zinc chloride in the concentration range of $1\times10^{-4}$M to $3\times10^{-4}$M. ANP receptor levels rise for 7–10 days, under optimal inducing conditions, $2\times10^{-4}$M $ZnCl_2$.

If desired, the ANP receptor secreted into the medium can be purified according to the procedures set forth above for the native protein, or by other standard methods known in the art.

Example VII

This example provides a protocol for the expression of intron-free DNA sequences encoding ANP receptor protein subunit in procaryotic systems.

A convenient host vector for expression is pKT52, which contains the "trc" promoter, followed by an ATG start codon. Briefly, the "trc" promoter contains the upstream portions of the trp promoter and the downstream, operator-containing, regions of the lac promoter and was originally prepared from two readily available plasmids containing these promoters. To construct the trc promoter as a BamHI/HindIII cassette, an intermediate plasmid pKK10-0 was prepared containing the hybrid promoter.

To prepare pKK10-0, pEA300 (Amman et al., (1983) Gene 25:167–178) was digested with PvuII and ClaI, filled in using dCTP only in the presence of DNA polymerase (Klenow), followed by digestion with mungbean nuclease, and the large vector fragment isolated. This vector fragment contains the upstream portions of the trp promoter. The fragment was ligated with a 55 bp blunt-ended HpaII/PvuII digest excised from pGL101 (Lauer et al., (1981) J. Mol. Appl. Genet. 1:139–147). which was prepared by digesting pGL101 with PvuII and HpaII followed by repair in the presence of dGTP and labeled dCTP. This fragment contains the lac operator region. The ligation product of these two blunt-end fragments was pKK10-0.

A BamHI site was inserted into pKK10-0 upstream of the trp/lac (trc) promoter/operator by digestion with EcoRI, filling in with Klenow, and insertion of the BamHI linker 5'-CCGGATCCGG-3'. The resulting plasmid, pKK10-1 was digested with PvuII, and ligated to the NcoI linker, 5'-ACCATGGT-3', digested with NcoI, filled in, and then ligated to a double-stranded linker containing PstI and HindIII sites provided as two complementary oligonucleotides, 5'-GCTGCAGCCAAGCTTGG-3' and its complement. The ligation mixture was used to transform *E. coli* to $Amp^R$. The isolated plasmid DNA was digested with BamHI and HindII, and the small BamHI/HindIII fragment obtained on electrophoresis contains the trc promoter.

To complete pKT52, the BamHI/HindIII fragment containing the trc promoter was ligated into the large fragment obtained from BamHI/HindIII digestion of pKK10-2 (Brosius, (1984) Gene 27:161–172) which contains the $Amp^R$ gene and the origin of replication. The resulting plasmid, pKK233-1 was digested to completion with PvuI and then partially with BglI and ligated with the 360 bp PvuI/BglI fragment containing the corresponding portion of the ampicillin resistance gene but lacking a PstI site from pUC8. The ligation mixture was used to transform *E. coli* and transformants were screened for the presence of only one PstI site next to the trc promoter. pKK233-2, which met the criteria, was digested with EcoRI and PvuII, filled in with dATP and dTTP, and religated to obtain the correct construction, pKT52, which contains the desired trc promoter, a downstream ATG start codon, and downstream NcoI, PstI and HindIII sites.

For construction of expression vectors, the receptor-encoding cDNA is obtained by excising with EcoRI or other appropriate enzyme digestion, and if necessary, modifying the appropriate fragment. The 3' end is prepared for insertion into pKT52 by cutting downstream of the termination codon at any convenient restriction site and supplying PstI or HindIII linkers. The 5' end is prepared by cutting at a site inside the coding sequence and supplying the missing codons and an NcoI site using a synthetic DNA, or by providing an appropriately located NcoI site by mutagenesis. The resulting NcoI/HindlII or NcoI/PstI fragment is then ligated into NcoI/HindIII-digested pKT52 or NcoI/PstI digested pKT52 to provide the ANP receptor-encoding cDNA in reading frame with the ATG start codon.

For bacterial expression, the resulting expression vectors are used to transform *E. coli* MC1061 or other appropriate host cells to $Amp^R$, and the transformed cells are then grown on M9 medium containing 1 mM IPTG for 3–5 hr to an O.D. of 0.2–0.5. (IPTG is a standard inducer for control sequences regulated by the lac operator.) The cells are then harvested, lysed by sonication or treatment with 5% trichloroacetic acid, and the cell extracts assayed for the desired ANP receptor protein. The receptor protein can be purified from the extracts by methods used for the native protein or by other procedures known in the art.

Example VIII

This example is directed to a method of probing a human genomic library to obtain clones encoding ANP receptor protein.

A human genomic library is prepared in λ Charon 4A, as described by Lawn et al., (1978) Cell 15:1157–1174. Portions of the cDNA inserts encoding bovine vascular ANP receptor (Example II) are prepared for use as probes by excising the cDNA from pANPR-1, and nick-translating the isolated insert, or some portion of it. The cDNA probes are hybridized to filters containing about 1 million recombinant phage from the library, as described for the 51-met probe in Example II, except that the hybridization mixture contains 40% formamide, and the filters are held at a constant 45° C. overnight. These filters are then washed twice for 1 hour at 65° C. in 2×SSC, 0.1% SDS. Recombinant phage containing human ANP receptor sequences are indicated by phage strongly hybridizing to the probe.

Related receptor genes can also be identified by using the same hybridization and wash conditions, except that the hybridization temperature is 35° C., and the wash temperature is 50° C. Strongly hybridizing positives containing genomic ANP receptor genes will remain, while weaker hybridizing probes indicate the related receptors.

If no positives appear, Southern hybridizations can be used to help define the appropriate screening conditions. First, Southern hybridizations are carried out with 10 μg of human DNA per lane, the human DNA being digested with various restriction enzymes (e.g., EcoRI, PstI, BamHI, and HindIII). Filters are then hybridized in the least stringent conditions (30% formamide) and washed under the lower stringency 50° C. wash described above. If the lanes in the Southern hybridization contain streaks of hybridization with no distinct bands above the background, the wash temperature is adjusted (up to 65° C.) until multiple bands appear.

Some bands will be stronger and some fainter, representing the gene for the homologous receptor and gene(s) for related receptors. respectively. More formamide (e.g., 40%) in the hybridization mixture of another Southern, followed by washing at the temperature found in the previous Southern, should reveal distinct bands with lowered background, with only the stronger bands showing. If the weaker bands are still showing, the formamide can be adjusted to a still higher concentration, for example, to 50%.

Mammalian genomic libraries, therefore, can be screened under appropriate conditions as defined in the above-described Southern hybridizations. Genomic coding sequences for ANP receptor protein isolated in the screening can then be employed in the expression protocol described in Example VI.

Example IX

This example provides a protocol useful for the production of monoclonal antibodies to ANP receptor protein.

Hybridomas can be prepared from B-cells which have been stimulated by antigen in tissue culture. First, thymocyte-conditioned medium is prepared. Two thymuses from 4–6 week old transgenic mice (e.g., Balb/c and C57) are incubated in a standard medium containing 1:1, DMEM-:RPMI medium supplemented with 1% (v/v) Nutricyte® (Enzymes International, San Diego). After 48 hr incubation, the medium is centrifuged at 2,000×g for 10 min and the cell pellet discarded. See generally Luben et al., (1980) Molec. Immunol. 17:635–639. One part thymocyte-conditioned medium is then combined with 2 parts of the standard medium supplemented with Nutricyte® to give a final volume of about 10 ml. Then 0.05–1.0 μg of purified ANP receptor protein is added (Example I). The combination is then incubated for 96 hr at 37° C. in a $CO_2$-humidified incubator. At the conclusion of incubation, activated B-cells are fused with an appropriate partner (e.g., P3X63Ag8.653 or Sp2/0-Ag14) to produce hybridomas by standard procedures. See, e.g., Kohler et al., (1975) Nature 256:485–496. Successful hybridomas are screened for production of the desired monoclonal antibodies by routine procedures. See, e.g., U.S. Pat. No. 4,562,003.

Example X

This example provides an assay for measuring ANP activity in a sample, such as human blood.

A frozen sample of pure receptor (Example I) is diluted in an appropriate buffer, such as 100 mM Tris, pH 7.5, 100 mM NaCl, 10 mM $CaCl_2$, 10 mM$MgCl_2$, 2 mg/ml $C_{12}E_8$, and the equivalent of approximately 0.5 pmol $^{125}$I-ANP binding sites is aliquoted per tube. Approximately 0.5 ml of binding buffer containing $^{125}$I-ANP (4.0 nM, spec. act.=200 cpm/fmol) is then added. A standard curve is constructed using various concentrations of unlabeled ANP (0.05–100.0 nM). Unknown samples are then added in place of unlabeled ANP. Separation of receptor-bound $^{125}$I-ANP from free ligand is accomplished by adding acetone (final concentration=37% v/v) followed by centrifugation at 500×g for 10 min at 4° C., followed by aspiration of the supernatant. The tubes can be counted on a gamma counter and a standard competition curve can be constructed (see FIG. 1).

Modifications of the above embodiments are readily apparent to and within the skill of the ordinary artisan. Thus, it is intended that the present invention be limited only by the scope of the appended claims.

I claim:

1. A composition comprising a recombinant DNA molecule encoding the amino acid sequence of the 60.5 kd bovine or the human ANP receptor protein subunit, said composition being free of DNA molecules that do not encode said amino acid sequence.

2. A recombinant DNA vector capable of transforming a selected host cell comprising a DNA coding sequence encoding the amino acid sequence of the 60.5 kd bovine or the human ANP receptor protein subunit, said coding sequence being oriented with respect to a heterologous DNA control sequence in said vector so that said coding sequence is transcribed in a host cell transformed by said vector.

3. A vector according to claim 2 wherein said host cell is procaryotic.

4. A vector according to claim 2 wherein said host cell is eucaryotic.

5. A procaryotic cell transformed by the vector of claim 3, or progeny thereof.

6. A nonmammalian eucaryotic cell line transformed by the vector of claim 4 or progeny thereof.

7. A mammalian cell line or progeny thereof transformed by a recombinant DNA vector capable of transforming said mammalian cell comprising a DNA coding sequence encoding the amino acid sequence of the 60.5 kd bovine or the human ANP receptor protein subunit, said coding sequence being oriented with respect to a DNA control sequence heterologous to said mammalian cell in said vector so that said coding sequence is transcribed in a host cell transformed by said vector.

8. A method of producing ANP receptor protein subunit comprising growing the cell of claim 5 under conditions whereby a peptide comprising ANP receptor protein subunit is expressed, and recovering said peptide.

9. A method of producing ANP receptor protein subunit comprising growing the cell of claim 6 under conditions whereby a peptide comprising ANP receptor protein subunit is expressed, and recovering said peptide.

10. A method of producing ANP receptor protein subunit comprising growing the cell line of claim 7 under conditions appropriate for said cell line whereby a peptide comprising the ANP receptor protein subunit is expressed, and recovering said peptide.

* * * * *